United States Patent
Burnett et al.

(10) Patent No.: US 7,423,149 B2
(45) Date of Patent: Sep. 9, 2008

(54) SUBSTITUTED N-ARYL AMIDINES AS SELECTIVE $D_1$ DOPAMINE RECEPTOR ANTAGONISTS FOR THE TREATMENT OF OBESITY AND CNS DISORDERS

(75) Inventors: Duane A. Burnett, Bernardsville, NJ (US); Wen-Lian Wu, Edison, NJ (US); Martin S. Domalski, Verona, NJ (US); Mary Ann Caplen, Sayreville, NJ (US); Richard Spring, Cranbury, NJ (US); Jean E. Lachowicz, Berkeley Heights, NJ (US)

(73) Assignee: Schering Corporation, Kenilworth, NJ (US)

( * ) Notice: Subject to any disclaimer, the term of this patent is extended or adjusted under 35 U.S.C. 154(b) by 247 days.

(21) Appl. No.: 11/018,990

(22) Filed: Dec. 21, 2004

(65) Prior Publication Data
US 2005/0137210 A1    Jun. 23, 2005

Related U.S. Application Data

(60) Provisional application No. 60/532,241, filed on Dec. 23, 2003.

(51) Int. Cl.
*C07D 241/04* (2006.01)
*C07D 295/00* (2006.01)
*C07D 211/00* (2006.01)
*C07C 257/00* (2006.01)

(52) U.S. Cl. ................... 544/358; 546/184; 564/244
(58) Field of Classification Search ............ None
See application file for complete search history.

(56) References Cited

U.S. PATENT DOCUMENTS 4,379,927 A * 4/1983 Vorbruggen et al. ........ 544/139

FOREIGN PATENT DOCUMENTS

WO    WO9924406    * 5/1999

OTHER PUBLICATIONS

Schnur, Rodney. Journal of Organic Chemistry, 1979, 44, 21, 3726-2727.*
Robeff, St. Doklady Bolgarskoi Akademii Nauk (1955), Volume Date 1954, 7(No. 3), 37-40. (based on CAPlus record).*
Robev. Doklady Bolgarskoi Akademii Nauk (1968), 21(11), 1181-3. (based on CAPlus record).*
Okubo et al. Journal of Physical Organic Chemistry, 1993, 6(9), 509-19. (based on CAPlus record).*
Borisy et al. Proceedings of the National Academy of Sciences, 2004, 100(13), 7977-82.*

* cited by examiner

*Primary Examiner*—James Wilson
*Assistant Examiner*—Noble Jarrell
(74) *Attorney, Agent, or Firm*—Palaiyur S. Kalyanaraman; William Y. Lee

(57) ABSTRACT

The present invention provides compounds, which, are novel antagonists for $D_1$ receptors as well as methods for preparing such compounds. In another embodiment, the invention provides pharmaceutical compositions comprising such $D_1$ receptor antagonists as well as methods of using them to treat CNS disorders, obesity, metabolic disorders, eating disorders such as hyperphagia, and diabetes.

7 Claims, No Drawings

SUBSTITUTED N-ARYL AMIDINES AS SELECTIVE $D_1$ DOPAMINE RECEPTOR ANTAGONISTS FOR THE TREATMENT OF OBESITY AND CNS DISORDERS

This application claims the benefit of priority of U.S. Ser. No. 60/532,241, filed on Dec. 23, 2003.

FIELD OF THE INVENTION

1. Field of the Invention

The present invention relates to n-aryl amidines useful as $D_1$ receptor antagonists, pharmaceutical compositions comprising the compounds, and methods of treatment using the compounds and compositions to treat obesity, metabolic disorders and CNS disorders.

2. Background of the Invention

Considerable research has been directed to treating obesity, nicotine addiction and substance abuse. The cost to society is very high from the health costs associated with obesity and addictions. Accordingly, it would be desirable to provide a substance which would suppress cravings for food, and other substances in a predisposed patient.

Substances which are administered to reduce craving should not produce significant physiological effects, such as stimulation of mood or elevate blood pressure or heart rate. This could result in the substitution of one abused substance for another. Compounds that dampen the desire for the abused substance also should not exacerbate the physiological symptoms of the abused substance in the event the individual relapses and takes the abused substance. Substances administered to reduce craving also should not produce significant adverse effects, such as dysphoria, restlessness or stiffness.

In addition to obesity and the disorders listed above, there is a strong need for drug therapy which can effectively treat, ameliorate and prevent central nervous system (CNS) disorders such as obsessive compulsive disorder, somatoform disorders, dissociative disorders, eating disorders, impulse control disorders, trichotillomania and autism. Obsessive-compulsive disorder ("OCD"), recognized to be among the most common of all psychiatric disorders, occurs in 2 to 3% of the U.S. population. OCD is characterized by anxiety-provoking and intrusive thoughts (e.g., fear of contamination and germs, doubt and uncertainty about future harm, need for symmetry, etc.), which lead to ritualistic and/or irrational behavior (e.g., constant checking, washing, touching, counting, etc.). See Hollander, et al., J. Clin. Psychiatry 57 (Suppl. 8), pp. 3-6 (1996).

Somatoform disorders (e.g., body dysmorphic disorder and hypochondriasis) are characterized by abnormal preoccupation with one's appearance or physical condition. For example, body dysmorphic disorder is a preoccupation with an imagined or slight defect in appearance. Many sufferers of body dysmorphic disorder are severely debilitated by their abnormal preoccupation, with significant impairment in social, occupational, or other important aspects of daily life. See Phillips, J. Clin. Psychiatry 57 (suppl. 8), pp. 61-64 (1996). Hypochondriasis is characterized by a persistent conviction that one is, or is likely to become ill. Many hypochondriacs are unable to work or engage in ordinary activities due to their preoccupation with illness.

Dissociative disorders (e.g., depersonalization) are characterized by sudden temporary alterations in identity, memory, or consciousness, segregating normally integrated memories or parts of the personality from the dominant identity of the individual. Depersonalization disorder, which is a dissociative disorder, is characterized by one or more episodes of depersonalization (feelings of unreality and strangeness in one's perception of the self or one's body image).

Eating disorders (e.g., anorexia nervosa, bulimia, and binge eating) are characterized by abnormal compulsions to avoid eating or uncontrollable impulses to consume abnormally large amounts of food. These disorders affect not only the social well-being, but also the physical well-being of sufferers.

Impulse control disorders (e.g., pathological gambling, compulsive buying, sexual compulsions and kleptomania) are characterized by a preoccupation with, and an inability to refrain from repeatedly engaging in various behaviors that are either socially unacceptable, or abnormally excessive by societal norms.

Trichotillomania is a habitual hair pulling that usually appears in children. See Merck Index, 15th Edition (1987); Christenson, Gary; O'Sullivan, Richard, Trichotillomania: Rational treatment options, CNS Drugs (1996), 6(1), 23-34; Tukel R; Keser V; Karali N T; Olgun T O; Calikusu C., Comparison of clinical characteristics in trichotillomania and obsessive-compulsive disorder, JOURNAL OF ANXIETY DISORDERS (2001 September-October), 15(5), 433-41; du Toit P L; van Kradenburg J; Niehaus D J; Stein D J, Characteristics and phenomenology of hair-pulling: an exploration of subtypes, COMPREHENSIVE PSYCHIATRY (2001 May-June), 42(3), 247-56.

Autism is a disorder characterized by a preoccupation with one's own self and a severe impairment of the ability to perceive or react to outside stimuli in a normal fashion. Many autistics are incapable of even communicating with others.

In view of the tragic and debilitating effects of these disorders, there is a strong need for a drug therapy which can effectively treat such disorders.

Dopamine is an important transmitter in the central and peripheral nervous system, critically regulating numerous neuropsychiatric and physiological functions. The actions of dopamine are mediated by five distinct receptor subtypes that are divided into two major subgroups, $D_1$-like and $D_2$-like. The $D_1$-like subfamily consists of the $D_1$ and $D_5$ subtypes. It has been demonstrated that $D_5$ dopamine receptors modulate neuronal pathways regulating blood pressure responses. Hollon, et al., Mice Lacking D5 Dopamine Receptors Have Increased Sympathetic Tone and are Hypertensive, THE JOURNAL OF NEUROSCIENCE, Dec. 14, 2002, 22(24): 10801-10810.

SUMMARY OF THE INVENTION

In its many embodiments, the present invention provides a novel class of n-aryl amidines as $D_1$ receptor antagonists, methods of preparing such compounds, pharmaceutical compositions comprising one or more such compounds, methods of preparing pharmaceutical compositions or formulations comprising one or more such compounds, and methods of treatment, prevention, inhibition or amelioration of obesity, metabolic disorders, CNS disorders or one or more diseases associated with obesity using such compounds or pharmaceutical compositions.

The compounds of the present invention may differentiate between human $D_1$ receptors (h $D_1$) and human $D_5$ receptors (h $D_5$).

In one aspect, the present application provides compounds having the general structure shown in formula I:

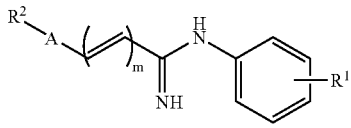

formula I or a pharmaceutically acceptable salt or solvates thereof, wherein

A is arylene or heteroarylene optionally substituted with 1 to 4 moieties which can be the same or different, each moiety being independently selected from the group consisting of halogen, alkyl, aryl, heteroaryl, heterocycloalkyl, cycloalkyl, —$CF_3$, —CN, —$OCF_3$, —$OR^{11}$, —$(CR^4R^5)_pOR^{11}$, —$NR^5R^6$, —$(CR^4R^5)_pNR^5R^6$, —$C(O_2)R^{11}$, —$C(O)R^{11}$, —$C(O)NR^5R^6$, —$SR^{11}$, —$S(O_2)R^{11}$, —$S(O_2)NR^5R^6$, —$N(R^5)S(O_2)R^7$, —$N(R^5)C(O)R^7$ and —$N(R^5)C(O)NR^5R^6$;

m is 0 or 1;

p is 1 to 4;

$R^1$ is 1 to 5 moieties independently selected from hydrogen, cycloalkyl, heterocyclyl, aryl, heteroaryl, halogen, hydroxy, alkoxy, —$NR^5R^6$, —$SR^{11}$, —$CF_3$, —$OCF_3$, —CN, —$NO_2$ and alkyl, or two adjacent $R^1$ moieties can be linked to form

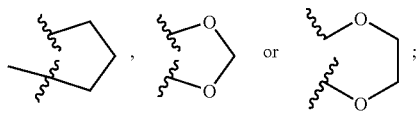

$R^2$ is 1 to 5 moieties independently selected from hydrogen, halogen, heteroaryl, heteroaralkyl, heterocycloalkyl, hydroxy, alkoxy, —$NR^3R^4$, —$OCF_3$, —$CF_3$, —$NO_2$, —CN, acyl, alkyl, $R^8$-substituted alkyl, aryl, heteroaryl, heteroaralkyl, heterocyclylalkyl,

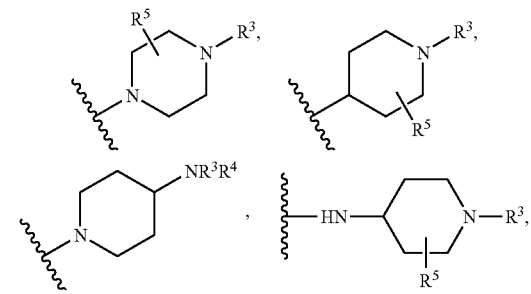

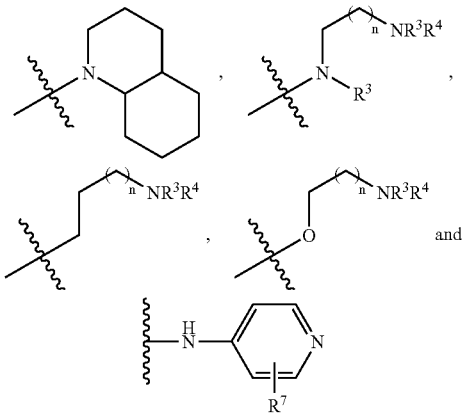

where n is 1 to 3, or two adjacent $R^2$ moieties can be linked to form

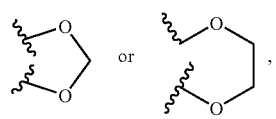

wherein each of said heteroaralkyl, heterocyclylalkyl, aryl or heteroaryl for $R^2$ can be optionally substituted with 1 to 4 moieties which can be the same or different, each moiety being independently selected from the group consisting of halogen, alkyl, aryl, cycloalkyl, alkylenyl, aralkyl, —C(O)H, —C(O)OH, —$C(R^4)$=$NOR^{11}$, —$CF_3$, —CN, —$OCF_3$, —$OR^{11}$, —$(CR^4R^5)_pOR^{11}$, —$NR^5R^6$, —$(CR^4R^5)_pNR^5R^6$, —$C(O_2)R^{11}$, —$C(O)R^{11}$, —$C(O)NR^5R^6$, —$SR^{11}$, —$S(O_2)R^{11}$, —$S(O_2)NR^5R^6$, —$N(R^5)S(O_2)R^7$, —$N(R^5)C(O)R^7$ and —$N(R^5)C(O)NR^5R^6$;

$R^3$ is hydrogen, alkyl, —$C(O)R^{11}$, —$SO_2R^{11}$, —$C(O)$ alkoxy, aryl, cycloalkyl, cycloalkylalkyl, heteroaryl, heterocyclylalkyl, heteroaralkyl or aralkyl, wherein each of said alkyl, aryl, cycloalkyl, cycloalkylalkyl, heteroaryl, heterocyclylalkyl, heteroaralkyl or aralkyl for $R^3$ can be optionally substituted with 1 to 4 moieties which can be the same or different, each moiety being independently selected from the group consisting of halogen, alkyl, aryl, cycloalkyl, —$CF_3$, —CN, —$OCF_3$, —$OR^{11}$, —$(CR^4R^5)_pOR^{11}$, —$NR^5R^6$, —$(CR^4R^5)_pNR^5R^6$, —$C(O_2)R^{11}$, —$C(O)R^{11}$, —$C(O)NR^5R^6$, —$SR^{11}$, —$S(O_2)R^{11}$, —$S(O_2)NR^5R^6$, —$N(R^5)S(O_2)R^7$, —$N(R^5)C(O)R^7$ and —$N(R^5)C(O)NR^5R^6$;

$R^4$ is hydrogen or alkyl;

$R^5$ is hydrogen, alkyl or aryl, wherein each of said alkyl or aryl for $R^5$ can be unsubstituted or substituted with 1 to 4 moieties which can be the same or different, each moiety being independently selected from the group consisting of —CN, —$NO_2$, halogen, vinyl, alkoxy, —$OCF_3$, alkoxyalkyl, —C(O)OH, —C(O)O-alkyl, —$CF_3$ and alkyl;

$R^6$ is hydrogen, alkyl or aryl, wherein each of said alkyl or aryl for $R^6$ can be unsubstituted or substituted with 1 to 4 moieties which can be the same or different, each moiety being independently selected from the group consisting of —CN, —$NO_2$, halogen, vinyl, alkoxy, —$OCF_3$, alkoxyalkyl, —C(O)OH, —C(O)O-alkyl, —$CF_3$ and alkyl;

$R^7$ is selected from the group consisting of alkyl, cycloalkyl, aryl, heteroaryl, —$CF_3$, —$OCF_3$, aralkyl and heteroaralkyl wherein each of said alkyl, cycloalkyl, aryl, heteroaryl, aralkyl and heteroaralkyl for $R^7$ can be unsubstituted or substituted with 1 to 4 moieties which can be the same or different, each moiety being independently selected from the group consisting of halogen, alkyl, aryl, cycloalkyl, —$CF_3$, —$OCF_3$, —CN, —$OR^5$, —$NR^5R^{10}$, —$CH_2OR^5$, —$C(O_2)R^5$, —$C(O)NR^5R^{10}$, —$C(O)R^5$, —$SR^{10}$, —$S(O_2)R^{10}$, —$S(O_2)NR^5R^{10}$, —$N(R^5)S(O_2)R^{10}$, —$N(R^5)C(O)R^{10}$ and —$N(R^5)C(O)NR^5R^{10}$;

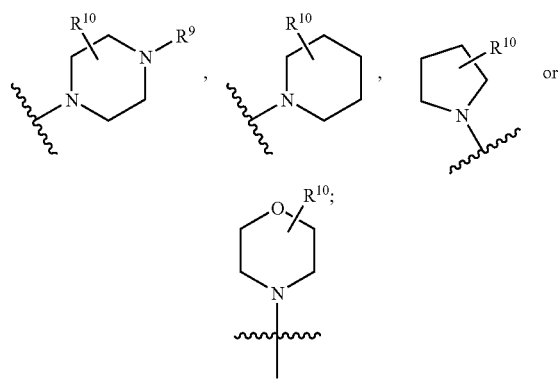

$R^8$ is alkyl, aryl, heteroaryl, —$NR^3R^4$, $R^9$ is hydrogen, alkyl, —$C(O)R^{11}$, —$SO_2R^{11}$, aryl, cycloalkyl, cycloalkylalkyl, heteroaryl, heterocyclyl, heteroaralkyl or aralkyl, wherein each of said aryl, cycloalkyl, cycloalkylalkyl, heteroaralkyl or aralkyl for $R^9$ can be unsubstituted or substituted with 1 to 4 moieties which can be the same or different, each moiety being independently selected from the group consisting of —CN, —$NO_2$, halogen, vinyl, alkoxy, —$OCF_3$, alkoxyalkyl, —C(O)OH, —C(O)O-alkyl, —$CF_3$ and alkyl;

$R^{10}$ is hydrogen, alkyl or aryl, wherein each of said alkyl or aryl for $R^{10}$ can be unsubstituted or substituted with 1 to 4 moieties which can be the same or different, each moiety being independently selected from the group consisting of —CN, —$NO_2$, halogen, vinyl, alkoxy, —$OCF_3$, alkoxyalkyl, —C(O)OH, —C(O)O-alkyl, —$CF_3$ and alkyl; and $R^{11}$ is alkyl or aryl, wherein each of said alkyl or aryl for $R^{11}$ can be unsubstituted or substituted with 1 to 4 moieties which can be the same or different, each moiety being independently selected from the group consisting of —CN, —$NO_2$, halogen, vinyl, alkoxy, —$OCF_3$, alkoxyalkyl, —C(O)OH, —C(O)O-alkyl, —$CF_3$ and alkyl.

The compounds of formula I can be useful as $D_1$ receptor antagonists and can be useful in the treatment of CNS disorders, metabolic disorders such as obesity and eating disorders such as hyperphagia. Another embodiment of this invention is directed to pharmaceutical compositions for the treatment of obesity which comprise an obesity treating amount of a compound of formula I, or a pharmaceutically acceptable salt or solvate of said compounds, and a pharmaceutically acceptable carrier therefore.

DETAILED DESCRIPTION OF THE INVENTION

In one embodiment, the present invention discloses compounds represented by structural formula I, or a pharmaceutically acceptable salt or solvate thereof, wherein the various moieties are as described as above.

In an embodiment of a compound of formula I, A is phenyl, quinolinyl, napthyl, pyridyl, indolyl or thiophenyl.

In another embodiment of a compound of formula I, m is 0.

In another embodiment of a compound of formula I, m is 1.

In another embodiment of a compound of formula I, $R^1$ is 1 or 2 moieties independently selected from hydrogen, cycloalkyl, heterocyclyl, aryl, heteroaryl, halogen, hydroxy, alkoxy, —$NR^5R^6$, —$SR^{11}$, —$CF_3$, —$OCF_3$, —CN, —$NO_2$ and alkyl, or two adjacent $R^1$ moieties can be linked to form

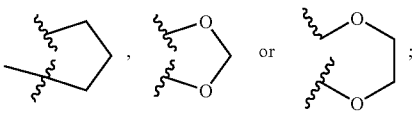

In another embodiment of a compound of formula I, $R^2$ is independently selected from halogen, alkyl, $R^8$-substituted alkyl, aryl, heteroaryl,

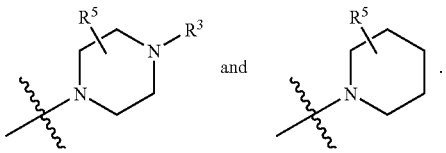

In another embodiment of a compound of formula I, $R^3$ is hydrogen or alkyl; and $R^5$ is hydrogen or alkyl.

In another embodiment of a compound of formula I, $R^3$ is methyl or hydrogen; and $R^5$ is methyl or hydrogen.

In another embodiment of a compound of formula I, A is phenyl, quinolinyl, napthyl, pyridyl, indolyl or thiophenyl; and m is 0.

In another embodiment of a compound of formula I, A is phenyl, quinolinyl, napthyl, pyridyl, indolyl or thiophenyl; and m is 1.

In another embodiment of a compound of formula I, where formula I is the following structural formula

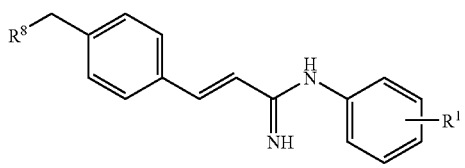

wherein $R^1$ is 1 to 5 moieties independently selected from hydrogen, cycloalkyl, heterocyclyl, aryl, heteroaryl, halogen, hydroxy, alkoxy, —$NR^5R^6$, —$SR^{11}$, —$CF_3$, —$OCF_3$, —CN, —$NO_2$ and alkyl, or two adjacent $R^1$ moieties can be linked to form

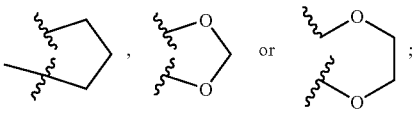

and $R^8$ is alkyl, aryl, heteroaryl, —$NR^3R^4$,

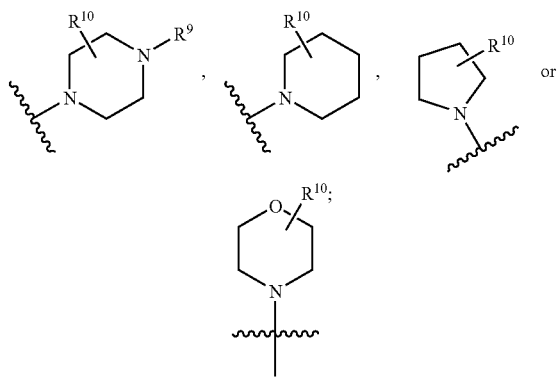

and $R^9$, $R^{10}$ and $R^{11}$ are as defined above.

In another embodiment of a compound of formula I, having the formula

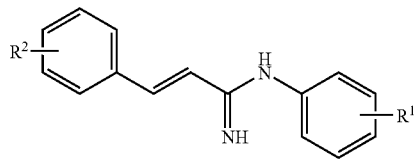

wherein $R^1$ is 1 to 5 moieties independently selected from hydrogen, cycloalkyl, heterocyclyl, aryl, heteroaryl, halogen, hydroxy, alkoxy, —$NR^5R^6$, —$SR^{11}$, —$CF_3$, —$OCF_3$, —$CN$, —$NO_2$ and alkyl, or two adjacent $R^1$ moieties can be linked to form

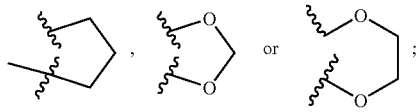

$R^2$ is 1 to 5 moieties independently selected from hydrogen, halogen, hydroxy, alkoxy, —$NR^3R^4$, —$OCF_3$, —$CF_3$, —$NO_2$, alkyl $R^8$-substituted alkyl, aryl, heteroaryl,

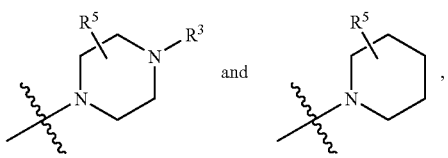

wherein each of said alkyl, aryl or heteroaryl for $R^2$ can be optionally substituted with 1 to 4 moieties which can be the same or different, each moiety being independently selected from the group consisting of halogen, alkyl, aryl, cycloalkyl, —$CF_3$, —$CN$, —$OCF_3$, —$OR^{11}$, —$(CR^4R^5)_pOR^{11}$, —$NR^5R^6$, —$(CR^4R^5)_pNR^5R^6$, —$C(O_2)R^{11}$, —$C(O)R^{11}$, —$C(O)NR^5R^6$, —$SR^{11}$, —$S(O_2)R^{11}$, —$S(O_2)NR^5R^6$, —$N(R^5)S(O_2)R^7$, —$N(R^5)C(O)R^7$ and —$N(R^5)C(O)NR^5R^6$;

p is 1 to 4;

$R^3$ is hydrogen or alkyl;

$R^4$ is hydrogen or alkyl;

$R^5$ is hydrogen or alkyl;

$R^6$ is hydrogen, alkyl or aryl;

$R^7$ is as defined as above;

and $R^{11}$ is alkyl or aryl.

In an additional embodiment of a compound of formula I, m is 1; A is aryl or heteroaryl; $R^1$ is halogen; $R^2$ is one or two moieties independently selected from halogen, —$NR^3R^4$, $R^8$-substituted alkyl, aryl, heteroaryl,

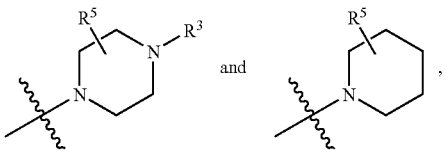

wherein said aryl or heteroaryl for $R^2$ can be optionally substituted with 1 to 4 moieties which can be the same or different, each moiety being independently selected from —$CN$ and —$C(O)H$; $R^3$ is hydrogen or alkyl; $R^4$ is hydrogen or alkyl; and $R^5$ is hydrogen or alkyl.

In an additional embodiment of a compound of formula I, A is phenyl; $R^1$ is chloro; $R^2$ is one or two moieties selected from the group consisting of indolyl, phenyl, $R^8$-substituted methyl, chloro, N(ethyl)$_2$,

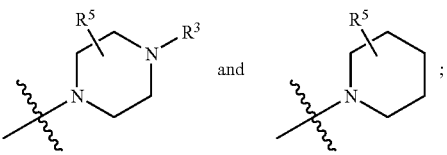

$R^3$ is hydrogen or methyl; $R^5$ is hydrogen or methyl and $R^8$ is as defined above.

In an additional embodiment of a compound of formula I, $R^1$ is in a position para to the parent moiety.

Other compounds of formula I include but are not limited to Examples 1-134.

An inventive group of compounds is shown in Table 1 below:

TABLE 1

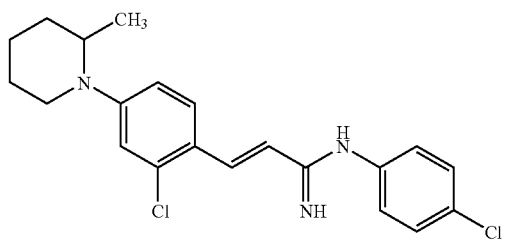

TABLE 1-continued

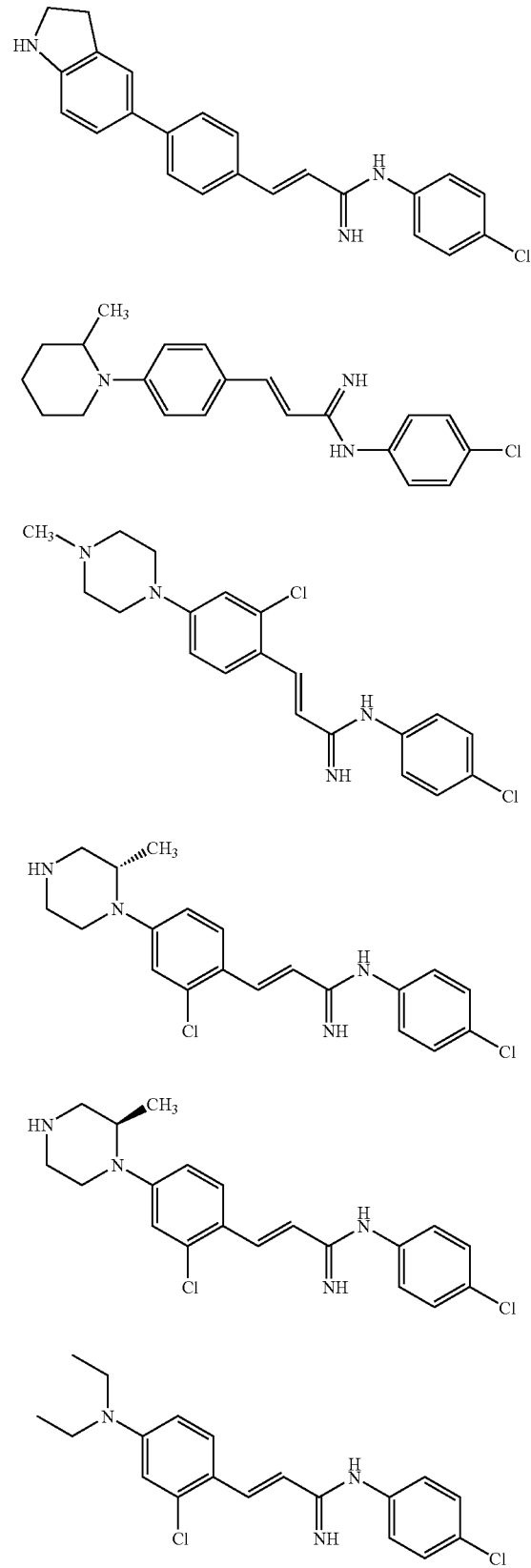

TABLE 1-continued

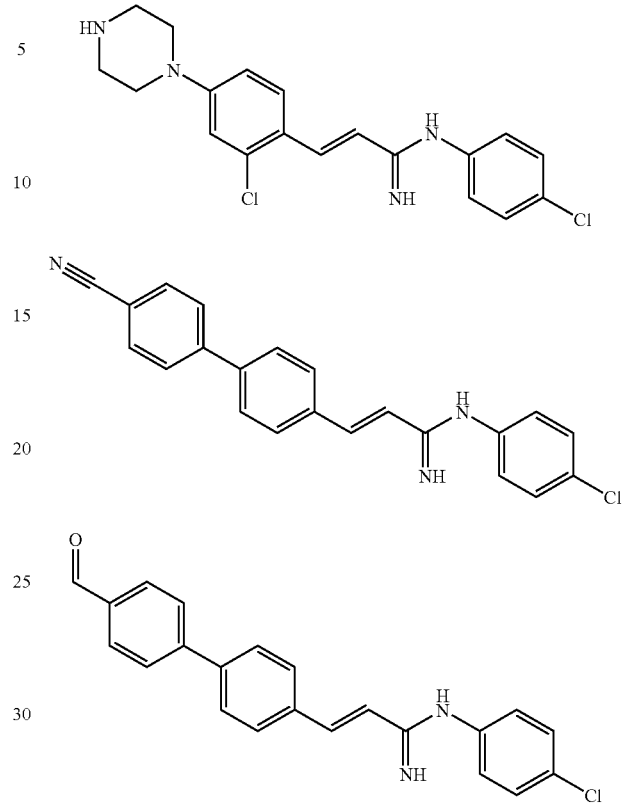

In yet another embodiment, the compound of formula I where said compound's binding affinity (Ki) for a human $D_1$ (h $D_1$) receptor is greater than said compound's binding affinity (Ki) for a human $D_5$ (h $D_5$) receptor such that [h $D_5$ Ki]/[h $D_1$ Ki] is greater than 100.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "cycloalkyl" and so forth.

As used above, and throughout the specification, the following terms, unless otherwise indicated, shall be understood to have the following meanings:

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)₂, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkylalkyl" means a cycloalkyl-alkyl group in which the cycloalkyl and alkyl group are previously described. The bond to the parent moiety is through the alkyl. Non-limiting examples of suitable cycloalkylalkyl groups include

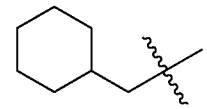

"Halo" means fluoro, chloro, bromo or iodo. Preferred are fluoro, chloro and bromo.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH₂, —C(=NH)—NH₂, —C(=NH)—NH(alkyl), Y₁Y₂N—, Y₁Y₂N-alkyl-, Y₁Y₂NC(O)—, Y₁Y₂NSO₂— and —SO₂NY₁Y₂, wherein Y₁ and Y₂ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH₃)₂— and the like which form moieties such as, for example:

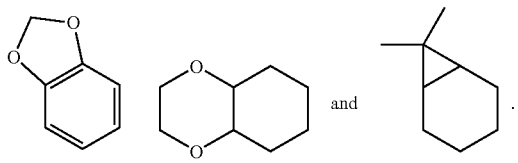

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

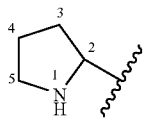

there is no —OH attached directly to carbons marked 2 and 5.

It should also be noted that tautomeric forms such as, for example, the moieties:

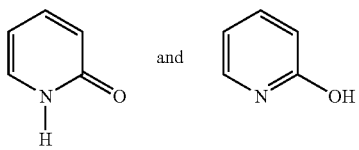

are considered equivalent in certain embodiments of this invention.

"Heterocyclylalkyl" means a heterocyclyl-alkyl group in which the heterocyclyl and alkyl group are previously described. The bond to the parent moiety is through the alkyl. Non-limiting examples of suitable heterocyclylalkyl groups include

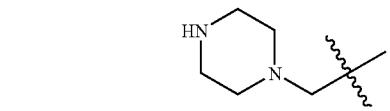

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkyl" means an alkoxy-alkyl group in which the alkoxy and alkyl groups are as previously described. The bond to the parent moiety is through the alkyl. Non-limiting examples of suitable groups include ethoxymethyl, ethoxyethyl, methoxymethyl and methoxymethyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group in which the alkoxy group is as previously described. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group in which the aryloxy group is as previously described. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group in which the aralkyl group is as previously described. Non-limiting example of a suitable aralkoxycarbonyl group is benzyloxycarbonyl. The bond to the parent moiety is through the carbonyl.

"Alkylsulfonyl" means an alkyl-S($O_2$)— group in which the alkyl group is as previously described. Preferred groups are those in which the alkyl group is lower alkyl. The bond to the parent moiety is through the sulfonyl.

"Arylsulfonyl" means an aryl-S($O_2$)— group in which the aryl group is as previously described. The bond to the parent moiety is through the sulfonyl.

"Heteroaralkylthio" means a heteroaralkyl-S— group in which the heteroaralkyl group is as previously described. A non-limiting example of a suitable heteroaralkylthio group is a pyridiylthio. The bond to the parent moiety is through the sulfur.

"Heteroarylsulfonyl" means a heteroaryl-S($O_2$)— group in which the heteroaryl group is as previously described. The bond to the parent moiety is through the sulfonyl.

"Heteroarylthio" means a heteroaryl-S— group in which the heteroaryl group is as previously described. The bond to the parent moiety is through the sulfur.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

Polymorphic forms of the compounds of Formula I and of the salts, solvates and prodrugs of the compounds of Formula I, are intended to be included in the present invention.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The compounds according to the invention have pharmacological properties; in particular, the compounds of Formula I can be highly selective, high affinity $D_1$ receptor antagonists useful for the treatment of obesity.

Another aspect of this invention is a method of treating a patient (e.g., human) having a disease or condition therapeutically treated by administering a therapeutically effective amount of at least one compound of formula I, or a pharmaceutically acceptable salt or solvate, of said compound to the patient.

A useful dosage is about 0.001 to 100 mg/kg of body weight/day of the compound of formula I. A preferred dosage is about 0.01 to 25 mg/kg of body weight/day of a compound of formula I, or a pharmaceutically acceptable salt or solvate of said compound.

Another aspect of this invention is directed to a method of treating obesity comprising administering to a patient in need of such treatment a therapeutically effective amount of at least one compound of formula I, or a pharmaceutically acceptable salt or solvate of said compound.

Another aspect of this invention is directed to a method for treating eating and metabolic disorders such as bulimia or anorexia comprising administering to a patient a therapeutically effective amount of at least one compound of formula I, or a pharmaceutically acceptable salt or solvate of said compound.

Another aspect of this invention is directed to a method for treating hyperlipidemia comprising administering to a patient a therapeutically effective amount of at least one compound of formula I, or a pharmaceutically acceptable salt or solvate of said compound.

Another aspect of this invention is directed to a method for treating cellulite and fat accumulation comprising administering to a patient a therapeutically effective amount of at least one compound of formula I, or a pharmaceutically acceptable salt or solvate of said compound.

Another aspect of this invention is directed to a method for treating type II diabetes comprising administering to a patient a therapeutically effective amount of at least one compound of formula I, or a pharmaceutically acceptable salt or solvate of said compound.

In addition to the "direct" effect of the compounds of this invention on the $D_1$ receptor, there are diseases and conditions that can benefit from weight loss such as insulin resistance, impaired glucose tolerance, Type II Diabetes, hypertension, hyperlipidemia, cardiovascular disease, gallstones, certain cancers, and sleep apnea.

The compounds of formula I are expected to be useful in the therapy of a patient suffering from obsessive compulsive disorder, a somatoform disorder, a dissociative disorder, an eating disorder, an impulse control disorder, or autism by administering an effective amount of a compound of formula I, or salt or solvate thereof.

More specifically the compounds of formula I can be useful in the treatment of a variety of eating disorders including (but not limited to) anorexia nervosa, bulimia, and binge eating.

Compounds of formula I can be useful in the treatment of a variety of impulse control disorders including (but not limited to) pathological gambling, trichotillomania, compulsive buying, and sexual compulsion.

The compounds of the invention (i.e., the compounds of formula I) may also be used in combinations with other compounds as described below. Accordingly, another aspect of this invention is a method for treating obesity comprising administering to a patient (e.g., a female or male human)

a. an amount of a first compound, said first compound being a compound of the invention, a solvate thereof, or a pharmaceutically acceptable salt of said compound or of said solvate; and b. an amount of a second compound, said second compound being an anti-obesity and/or anorectic agent such as a $\beta_3$ agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising a. a first compound, said first compound being a compound of the invention, a solvate thereof, or a pharmaceutically acceptable salt of said compound or of said solvate; and
b. a second compound, said second compound being an anti-obesity and/or anorectic agent such as a $\beta_3$ agonist, a thyromimetic agent, an anoretic, or an NPY antagonist; and/or optionally a pharmaceutical carrier, vehicle or diluent.

Another aspect of this invention is a kit comprising:
a. an amount of a compound of the invention, a solvate thereof, or a pharmaceutically acceptable salt of said compound or of said solvate and a pharmaceutically acceptable carrier, vehicle or diluent in a first unit dosage form;
b. an amount of an anti-obesity and/or anorectic agent such as a $\beta_3$ agonist, a thyromimetic agent, an anoretic agent, or an NPY antagonist and a pharmaceutically acceptable carrier, vehicle or diluent in a second unit dosage form; and
c. means for containing said first and second dosage forms wherein the amounts of the first and second compounds result in a therapeutic effect.

Preferred anti-obesity and/or anorectic agents (taken singly or in any combination thereof) in the above combination methods, combination compositions and combination kits include: phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes comprising administering to a patient (e.g., a female or male human)
a. an amount of a first compound, said first compound being a compound of the invention, a solvate thereof, or a pharmaceutically acceptable salt of said compound or of said solvate; and
b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of the invention, a solvate thereof, or a pharmaceutically acceptable salt of said compound or of said solvate; a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:
a. an amount of a compound of the invention, a solvate thereof, or a pharmaceutically acceptable salt of said compound or of said solvate and a pharmaceutically acceptable carrier, vehicle or diluent in a first unit dosage form;
b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and
c. means for containing said first and second dosage forms wherein the amounts of the first and second compounds result in a therapeutic effect.

For combination treatment with more than one active agent, where the active agents are in separate dosage formulations, the active agents may be administered separately or in conjunction. In addition, the administration of one element may be prior to, concurrent to, or subsequent to the administration of the other agent.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The dosage regimen utilizing the compounds of formula I or their pharmaceutical compositions of the present invention, is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compounds of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.01 mg/kg to 500 mg/kg of bodyweight. The range is more particularly from about 0.01 mg/kg to 150 mg/kg of body weight per day or most particularly 0.01 mg/kg to 10 mg/kg.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following solvents and reagents may be referred to by their abbreviations in parenthesis:
Triethylamine: TEA
m-methylphenylboronic acid: ArB(OH)$_2$
Tetrahydrofuran: THF
Methoxylamine hydrochloride: MeONH$_2$ HCl
Iodomethane: MeI
Triphenylphosphine: PPh$_3$
N,N-dimethylformamide: DMF
Dimethylsulfoxide: DMSO
Thiocarbonyldiimidazole; TCDI
Tetrahydrofuran: THF
para-toluenesulfonic acid: p-TsOH or p-TSA
Mass Spectrum: MS
Nuclear Magnetic Resonance spectroscopy; NMR
room temperature (ambient) about 25° C. (rt).

A synthetic route of these amidines is illustrated in Scheme 1. In Method A, 4-fluoro-2-chlorobenzaldehyde (or other fluoro-substituted benzaldehyde) can be reacted with nucleophilic amines, such as N-Boc-piperazine to give nucleophilic aromatic substitution product where fluorine has been replaced. In Method B, the aldehyde is then reacted with stabilized Wittig reagent, cyanomethyl triphenylphosphonium chloride, and base to give a mixture of E and Z olefin products. In Method C, the amidine is formed by the reaction of trimethyl aluminate of an appropriately substituted aniline with the nitrile from the preceding reaction. Deprotection of the Boc group in Method D gave the corresponding free piperazine. Substitution of this piperazine can be accomplished by reduction amination (Method E), acylation (Method F), or sulfonylation (Method G). Alternatively, more highly substituted piperazines can be used in Method A.

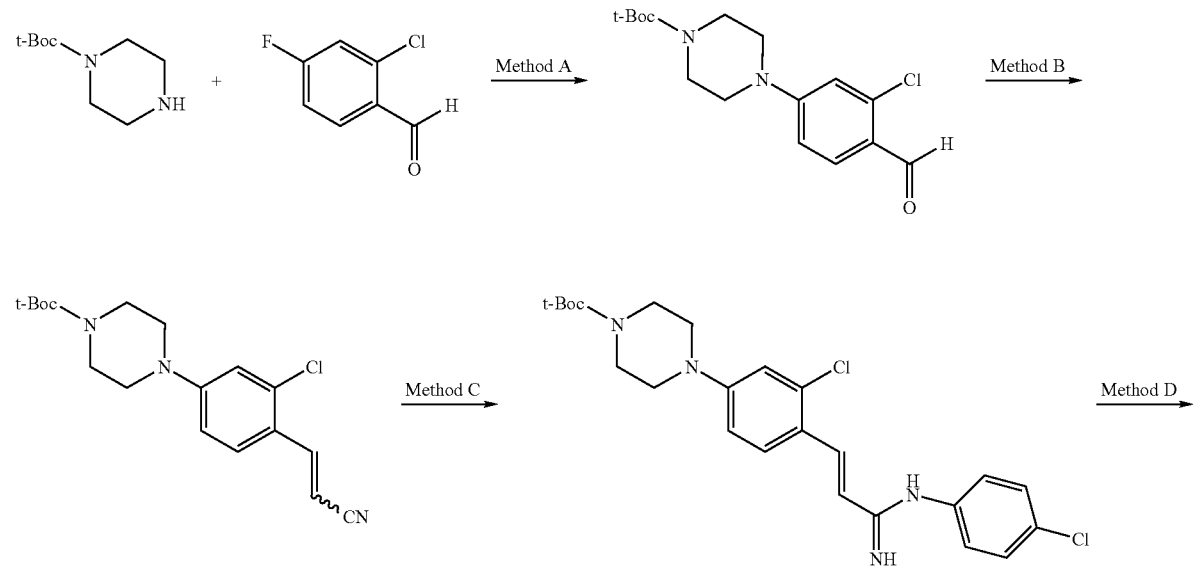

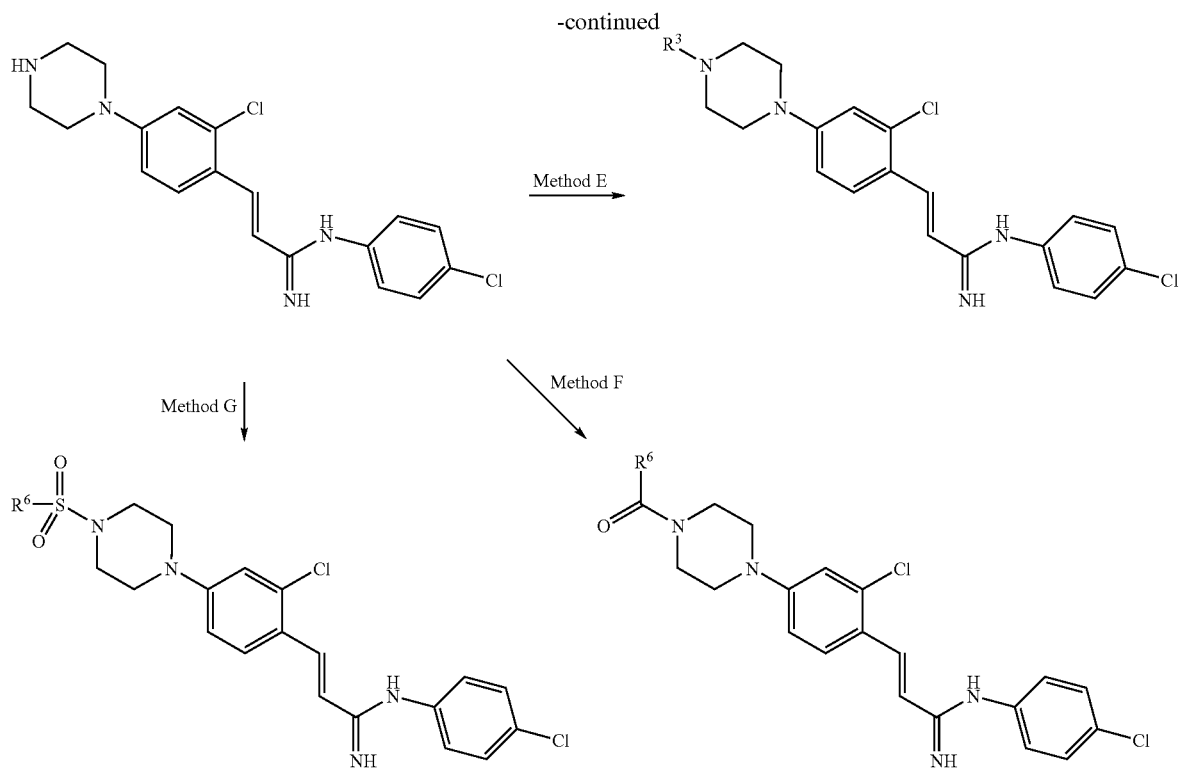

For amidines of structure II, analogous chemistry to that shown in scheme 1 can be sued. Palladium mediated aminations (Scheme 2, method H) can be used as an alternative to nucleophilic aromatic substitution (method A).

Scheme 2

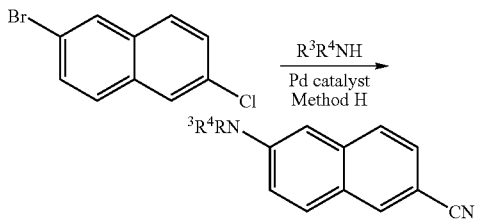

A synthetic route of amidines of type III is illustrated in Scheme 3. In Method I, 4-bromobenzaldehyde can be protected as its dimethyl acetal and the corresponding Grignard reagent prepared. Condensation of the Grignard reagent with aldehydes generates the benzylic alcohols. Two step free radical deoxygenation is accomplished in Method J. Deprotection and continuation of the scheme with homologation (Method B) and amidine formation (Method C) completes the synthesis.

Alternatively, the alcohol intermediate can be prepared from the $R^8$-Griganard reagent and a monoprotected terphthalaldehyde as shown in Scheme 4 (Method K).

Scheme 3

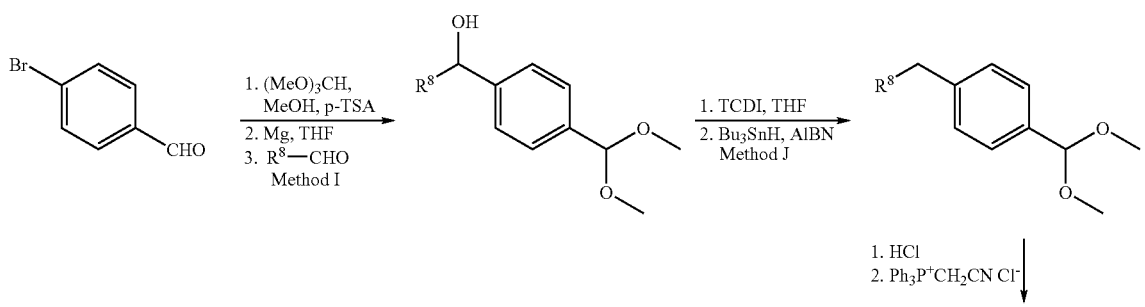

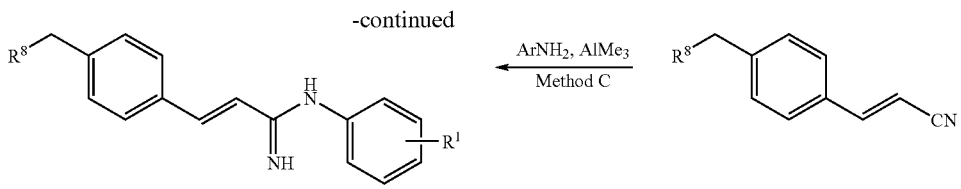

Scheme 4

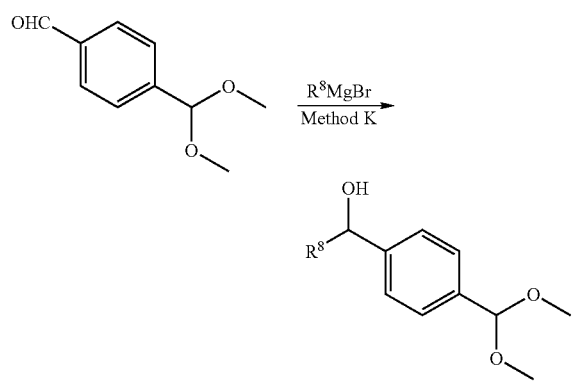

Method A: 2-chloro-4-(N-t-Boc-piperazinyl)benzaldehyde: To 5.00 g (31.5 mmol) of 2-chloro-4-fluorobenzaldehyde in 75 mL of dry N,N-dimethylacetamide was added 11.7 g (31.5 mmol) of N-Bocpiperazine. The reaction was heated to 140° C. under nitrogen for 3 h, then stirred overnight at room temperature. The solvent was removed in vacuo and the mixture partitioned between water and ethyl acetate. The organic layer was washed with brine, dried over $MgSO_4$, and concentrated to give an orange solid (14.64 g). The crude material was chromatographed over $SiO_2$ eluting with 10-20% ethyl acetate in hexanes to give 8.94g (87%) of the desired aldehyde as a yellow solid.

$^1$HNMR (DMSO-d6) δ: 10.30 (2, 1H), 7.82 (d, J=10 Hz 1 H), 67.77-6.79 (m, 2H), 3.59 (t, J=5 Hz, 4H), 3.39 (t, J=5 Hz, 4H), 1.50 (s, 9H)

Method B: 2-[2-Chloro-4-(N-Boc-piperazin-1-yl)phenyl] acrylonitrile: To 12.09 g (35.75 mmol) of cyanomethyltriphenyl phosphonium chloride in 160 mL of dry tetrahydrofuran cooled to −78° C. was added 36.0 ML of 1 N hexamethyldisilazide. The reaction was stirred for 1h, followed by the dropwise addition of 8.94 g (27.5 mmol) of 2-chloro-4-(N-t-Boc-piperazinyl) benzaldehyde in 150 ML of dry tetrahydrofuran. The reaction as warmed to 0° C. then quenched with water and extracted with dichloromethane. The organic layer was dried over $MgSO_4$, and concentrated to give an orange solid (23.4 g). The crude material was chromatographed over $SiO_2$ eluting with 10-15% ethyl acetate in hexanes to give 4.13 g (43%) of desired aldehyde as a light yellow solid.

$^1$HNMR (DMSO-dg) δ: 8/16 (d, J=9Hz, 1H), 7.45 (d, J=12Hz, 1H), 6.88 (d, J=3Hz, 1H), 6.82 (dd, J=3, 9Hz, 1H), 6.35 (d, J=12Hz, 1H), 3.58 (t, J=5Hz, 4H), 3.29 (t, J=5Hz, 4H), 1.49 (s, 9H)

Method C: (E)-N-(4-Chlorophenyl)-3-[2-chloro-4-(N'-Boc-piperzain-1-yl]-2-propenimidamide: To 12.85 mL (26 mmol) of trimethylaluminum in 75 Ml dry toluene under nitrogen was added 3.28 g (26 mmol) of 4-chloroaniline in 50 mL dry toluene. The mixture was stirred for 45 minutes followed by the addition of 4.13 g (11.8 mmol) of 2-[2-chloro-4-(N-Boc-piperazin-1-yl)phenyl]acrylonitrile in 50 mL of dry toluene. The reaction was heated to 80° C. overnight. The reaction was cooled to room temperature and quenched with $NaSO_4$•$(H_2O)_{10}$. When evolution of gas ceased, the reaction was filtered and concentrated in vacuo to give 7.26 g of an orange oil. The crude material wash chromatographed twice over $SiO_2$ eluting with 5% methanol in dichloromethane to give 3.47 (62%) of the desired amidine as yellow foamy solid. Mp=138-140° C.

Method D: (E)-N-(4-Chlorophenyl)-3-[2-chloro-4(piperazin-1-yl)phenyl]-2-propenimidamide: To 1.00 g (2.1 mmol) of (E)-N-(4-Chlorophenyl)-3-[2-chloro-4-(N'-Boc-piperazin-1-yl)phenyl]2-propenimidamide in 20 mL dichloromethane was added 5 mL of 30% trifluoroacetic acid in dichloromethane. The mixture stirred for ~1 h. The reaction was partitioned between water and Dichloromethane. The dichloromethane layer was made basic with 1 N NaOH. The aqueous layer was extracted with dichloromethane and the combined organic layers were dried over $Na_2SO_4$ and concentrated in vacuo to give 0.76 g (79%) of the desired product as a yellow foamy solid. EI MS m/z=375 (M+1)+, mp=175° C. (d).

Method E, F, G: The distal piperazine nitrogen can be functionalized by standard reductive alkylation, acylation or sulfonylation chemistry.

Scheme 5:

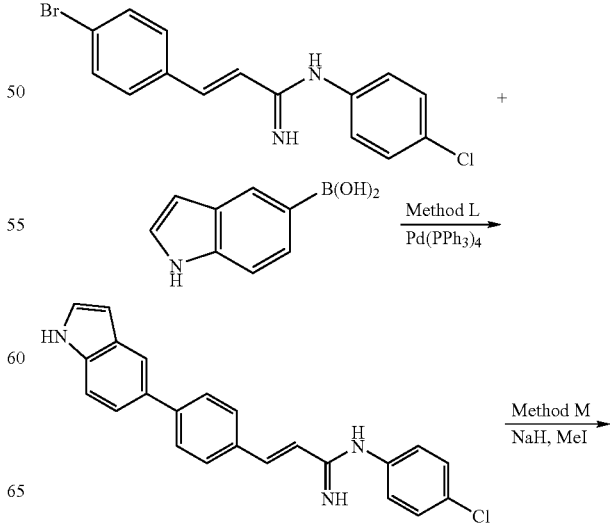

-continued

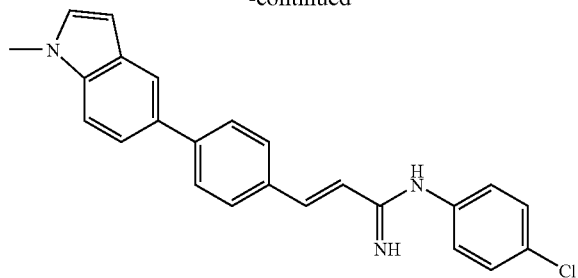

Method L: A mixture of 0.075 g (0.22 mmol) of 3-(4-bromo-phenyl)-N-(4-chloro-phenyl)-acrylamidine, 0.042 g (0.26 mmol) of 5-indoleboronic acid, and 0.013 g (0.011 mmol) of Pd(PPh$_3$)$_4$ in 3 mL of DME/water/ethanol (4/2/1) in a sealed tube was heated under microwave (45 W, 5 min). The reaction was diluted with 10 mL of saturated NaHCO$_3$, and extracted with three 10 mL portions of ethyl acetate. The combined organic extracts were washed with 10 mL of brine, dried over Na$_2$SO$_4$, filtered and concentrated. The residue was purified by preparative TLC eluting with 60% ethyl acetate in hexanes plus 1% NH$_4$OH to give 0.036 g of N-(4-chloro-phenyl)-3-[4-(1H -indol-5-yl)-phenyl]-acrylamidine.

Method M: To a stirred solution of 0.10 g (0.27 mmol) of N-(4-chloro-phenyl)-3-[4-(1H -indol-5-yl)-phenyl]-acrylamidine in 3 mL of DMF was added 0.011 g (0.28 mmol) of 60% NaH at 0° C. After 1 h, 0.018 mL (0.28 mmol) of iodomethane was introduced, the reaction was warmed to room temperature overnight and quenched with 10 mL of saturated NaHCO$_3$. It was extracted with three 10 mL portions of dichloromethane. The combined organic extracts were washed with 10 mL of brine, dried over Na$_2$SO$_4$, filtered and concentrated. The residue was chromatographed eluting with 40% ethyl acetate in hexanes to give 0.028 g of N-(4-chloro-phenyl)-3-[4-(1-methyl-1H-indol-5-yl)-phenyl]-acrylamidine.

Scheme 6:

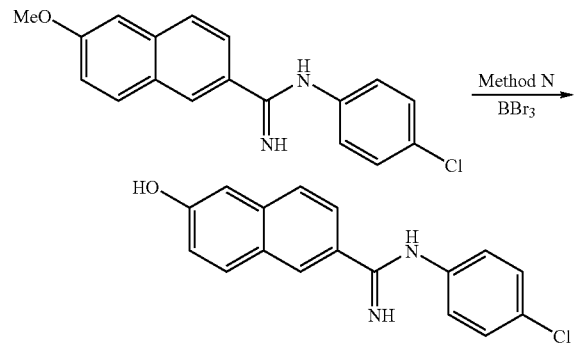

Method N: To a suspension of 0.104 g (0.33 mmol) of N-(4-chloro-phenyl)-6-methoxy -naphthalene-2-carboxamidine in 5 mL of dichloromethane was added 1.5 mL (1 M, 1.5 mmol) of BBr$_3$ in dichloromethane at 0° C. It was warmed to room temperature overnight, poured into 125 mL of saturated NaHCO$_3$ and extracted with three 50 mL portions of ethyl acetate. The combined organic extracts were washed with 125 mL of brine, dried over Na$_2$SO$_4$, filtered and concentrated. The residue was purified by preparative TLC eluting with 50% ethyl acetate in hexanes plus 1% NH$_4$OH to give 0.014 g of N-(4-chloro-phenyl)-6-hydroxy-naphthalene-2-carboxamidine.

Scheme 7:

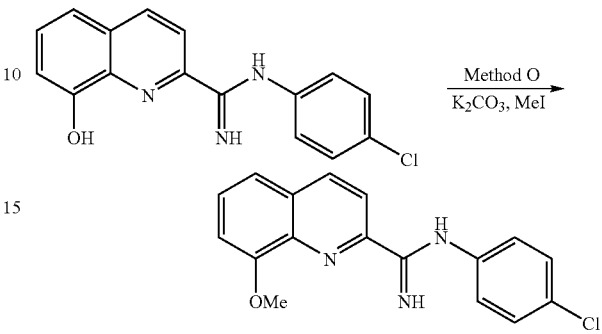

Method O: A mixture of 0.10 g (0.33 mmol) of N-(4-chloro-phenyl)-8-hydroxy -quinoline-2-carboxamidine, 0.137 g (1 mmol) of K$_2$CO$_3$ and 0.021 g (0.33 mmol) of iodomethane in 3.5 mL of DMF was heated under microwave (100 W, 5 min). It was diluted with 20 mL of NaHCO$_3$, extracted with three 10 mL portions of ether. The combined organic extracts were washed with 10 mL of brine, dried over Na$_2$SO$_4$, filtered and concentrated. The residue was purified by preparative TLC eluting with 20% ethyl acetate in hexanes to give 0.047 g of N-(4-chloro-phenyl)-8-methoxy -quinoline-2-carboxamidine.

Scheme 8:

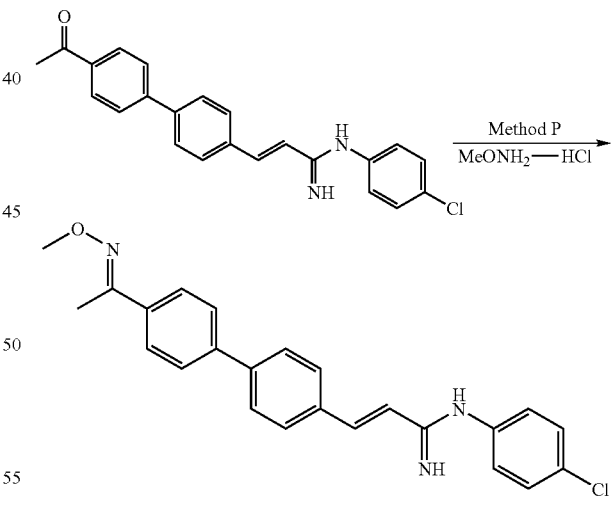

A mixture of 0.04 g (0.11 mmol) of 3-(4'-acetyl-biphenyl-4-yl)-N-(4-chloro-phenyl) -acrylamidine, 0.028 g (0.33 mmol) of methoxylamine hydrochloride and 0.027 g (0.33 mmol) of sodium acetate in 3 mL of methanol was heated under microwave (100 W, 5 min). Diluted with 20 mL of NaHCO$_3$, it was extracted with two 10 mL portions of ethyl acetate. The combined organic extracts were washed with 10 mL of brine, dried over Na$_2$SO$_4$, filtered and concentrated. The residue was purified by preparative TLC eluting with 70% ethyl acetate in hexanes plus 1% NH₄OH to give 0.004 g of N-(4-chloro-phenyl)-3-[4'-(1-methoxyimino-ethyl)-biphenyl-4-yl]-acrylamidine.

Scheme 9:

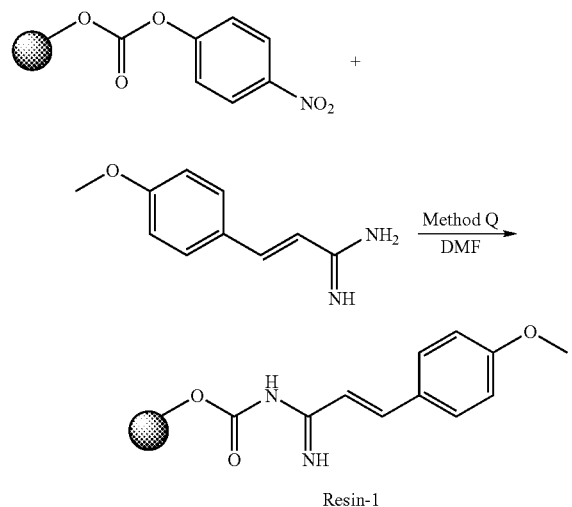

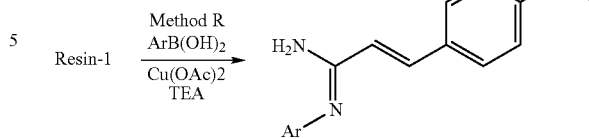

Method Q: To a pre-swelled p-nitrophenylcarbonate resin (550 mg, 0.64 mmol/g, 1 eq) in 5 ml DMF was added 3-(4-Methoxy-phenyl)-acrylamidine (2.4 eq) and 0.2 mL of diisopropylethyl amine. The mixture was shaken overnight before the resin was washed with dichloromethane, methanol and THF and dried in vacuo to give resin-1.

Method R: To a pre-swelled resin-1 (200 mg, 1 eq) in 2mL of anhydrous dichloromethane was added m-methylphenylboronic acid (5 eq), anhydrous copper acetate (2.5 eq) and triethylamine (0.5 ml). The reaction mixture was shaken overnight before the resin was washed with dichloromethane, methanol and THF. The resin was then treated with 40% TFA in dichloromethane for 30 min followed by filtration and wash with dichloromethane. The combined organic solutions were evaporation and residue purified via silica gel TLC plate to give desired N-aryl amidine 17. MW calculated for $C_{17}H_{18}N_2O$=266.3, observed m/z=267.1.

Table of Synthetic Methods and Analysis of Products:

| Ex | Chemical Structure | Synthetic Method | Formula | Calcd Mass | Obsd mass |
|---|---|---|---|---|---|
| 1 | 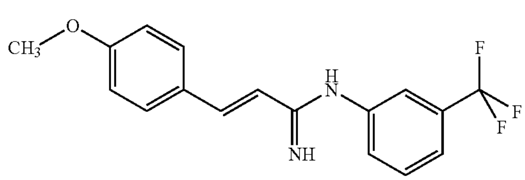 | R | $C_{17}H_{15}F_3N_2O$ | 320.3 | 321.1 |
| 2 | 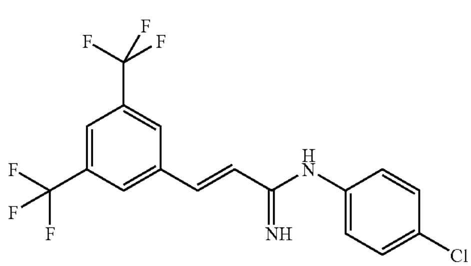 | C | $C_{17}H_{11}ClF_6N_2$ | 392.7 | 393.1 |
| 3 | 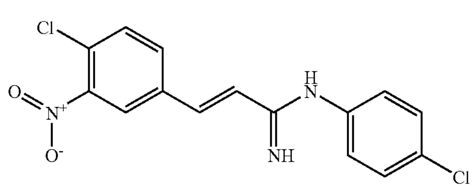 | C | $C_{15}H_{11}Cl_2N_3O_2$ | 336.2 | 336.0 |

-continued

Table of Synthetic Methods and Analysis of Products:

| Ex | Chemical Structure | Synthetic Method | Formula | Calcd Mass | Obsd mass |
|---|---|---|---|---|---|
| 4 | (4-trifluoromethoxyphenyl)-CH=CH-C(=NH)-NH-(4-chlorophenyl) | C | $C_{16}H_{12}ClF_3N_2O$ | 340.7 | 341.1 |
| 5 | (2-iodophenyl)-CH=CH-C(=NH)-NH-(4-chlorophenyl) | C | $C_{15}H_{12}ClIN_2$ | 382.6 | 383.1 |
| 6 | (4-(piperidin-1-ylmethyl)phenyl)-CH=CH-C(=NH)-NH-(4-chlorophenyl) | C | $C_{21}H_{24}ClN_3$ | 353.9 | 354.1 |
| 7 | (4-tert-butylphenyl)-CH=CH-C(=NH)-NH-(4-chlorophenyl) | C | $C_{19}H_{21}ClN_2$ | 312.8 | 313.1 |
| 8 | (4-(pyridin-3-ylmethyl)phenyl)-CH=CH-C(=NH)-NH-(4-hydroxyphenyl) | C + Bu4NF | $C_{21}H_{19}N_3O$ | 329.4 | 330.1 |
| 9 | (4-(pyridin-3-ylmethyl)phenyl)-CH=CH-C(=NH)-NH-(3-chloro-4-methoxyphenyl) | C | $C_{22}H_{20}ClN_3O$ | 377.9 | 378.1 |

-continued
Table of Synthetic Methods and Analysis of Products:
| Ex | Chemical Structure | Synthetic Method | Formula | Calcd Mass | Obsd mass |
|---|---|---|---|---|---|
| 10 | 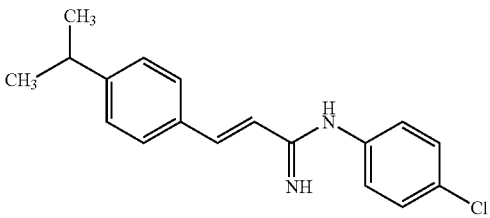 | C | $C_{18}H_{19}ClN_2$ | 298.8 | 299.2 |
| 11 | 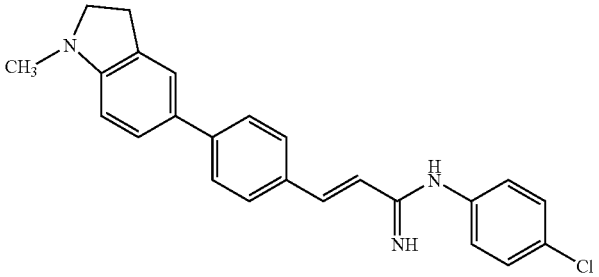 | L | $C_{24}H_{20}ClN_3$ | 385.9 | 386.1 |
| 12 | 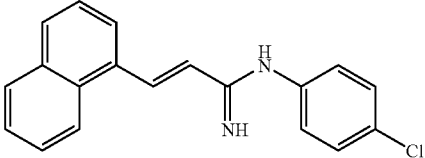 | C | $C_{19}H_{15}ClN_2$ | 306.8 | 307.1 |
| 13 | 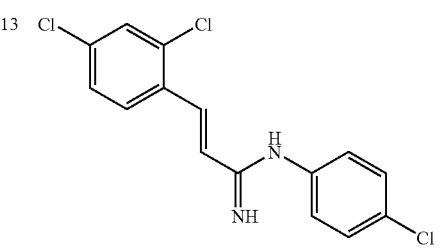 | C | $C_{15}H_{11}Cl_3N_2$ | 325.6 | 327.1 |
| 14 | 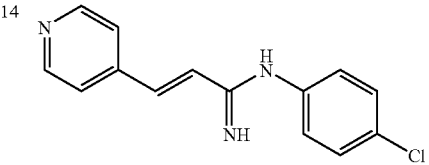 | C | $C_{14}H_{12}ClN_3$ | 257.7 | 258.1 |
| 15 | 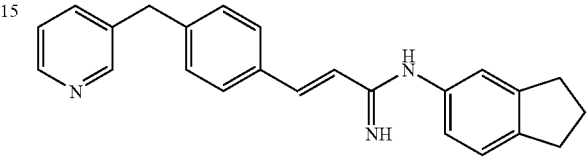 | C | $C_{24}H_{23}N_3$ | 353.5 | 354.1 |

-continued

Table of Synthetic Methods and Analysis of Products:

| Ex | Chemical Structure | Synthetic Method | Formula | Calcd Mass | Obsd mass |
|---|---|---|---|---|---|
| 16 | 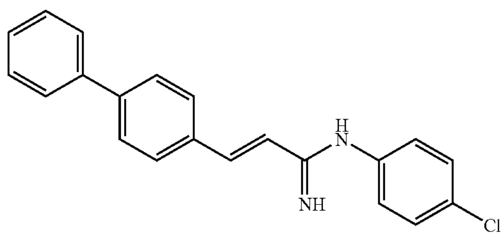 | C | $C_{21}H_{17}ClN_2$ | 332.8 | 333.1 |
| 17 | 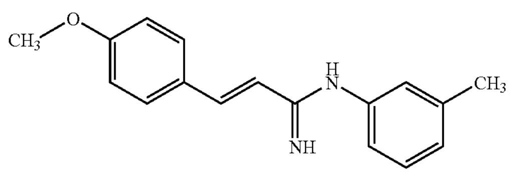 | R | $C_{17}H_{18}N_2O$ | 266.3 | 267.1 |
| 18 | 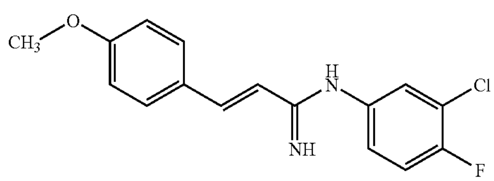 | R | $C_{16}H_{14}ClFN_2O$ | 304.8 | 305.1 |
| 19 | 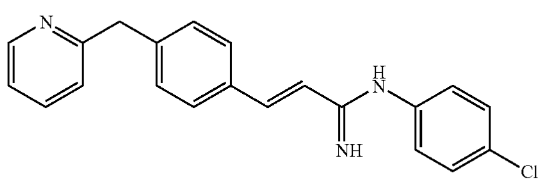 | C | $C_{21}H_{18}ClN_3$ | 347.8 | 348.1 |
| 20 | 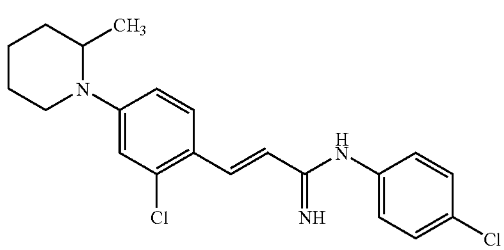 | C | $C_{21}H_{23}Cl_2N_3$ | 388. | 388.1 |
| 21 | 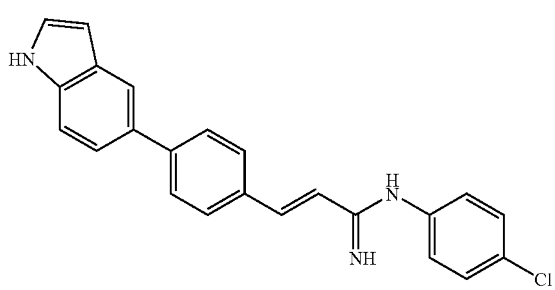 | L | $C_{23}H_{18}ClN_3$ | 371.9 | 372.1 |
| 22 | 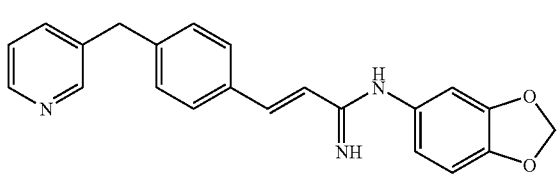 | C | $C_{22}H_{19}N_3O_2$ | 357.4 | 358.1 |

-continued

Table of Synthetic Methods and Analysis of Products:

| Ex | Chemical Structure | Synthetic Method | Formula | Calcd Mass | Obsd mass |
|----|--------------------|------------------|---------|------------|-----------|
| 23 | 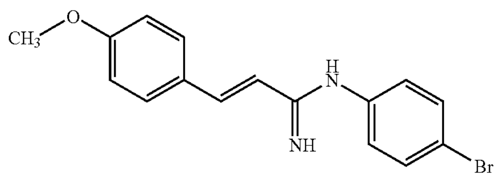 | R | $C_{16}H_{15}BrN_2O$ | 331.2 | 331.1 |
| 24 | 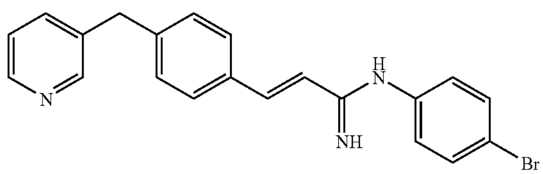 | C | $C_{21}H_{18}BrN_3$ | 392.3 | 394.1 |
| 25 | 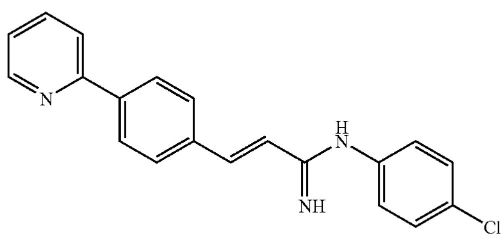 | C | $C_{20}H_{16}ClN_3$ | 333.8 | 334.1 |
| 26 | 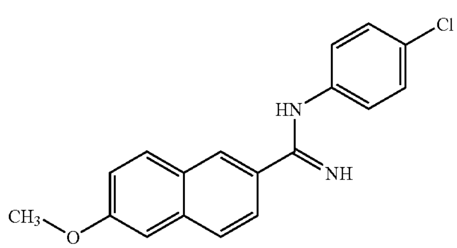 | C | $C_{18}H_{15}ClN_2O$ | 310.8 | 311.1 |
| 27 | 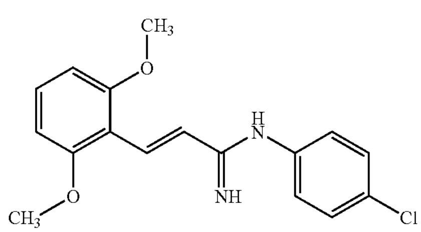 | C | $C_{17}H_{17}ClN_2O_2$ | 316.8 | 317.1 |
| 28 | 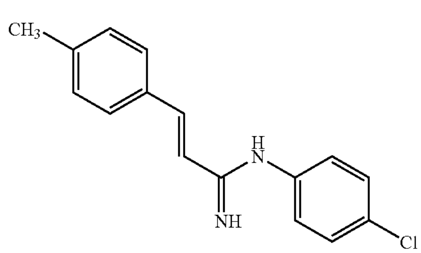 | C | $C_{16}H_{15}ClN_2$ | 270.8 | 271.0 |

-continued

Table of Synthetic Methods and Analysis of Products:

| Ex | Chemical Structure | Synthetic Method | Formula | Calcd Mass | Obsd mass |
|---|---|---|---|---|---|
| 29 | 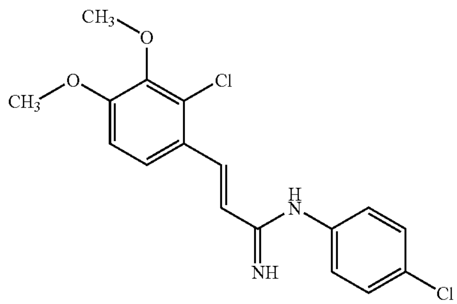 | C | C$_{17}$H$_{16}$Cl$_2$N$_2$O$_2$ | 351.2 | 351.1 |
| 30 | 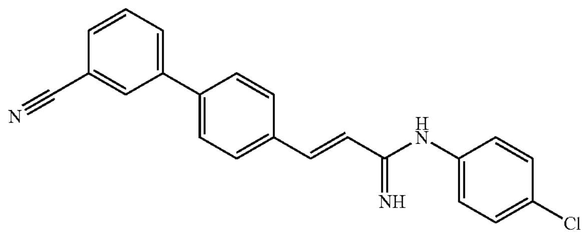 | L | C$_{22}$H$_{16}$ClN$_3$ | 357.8 | 358.1 |
| 31 | 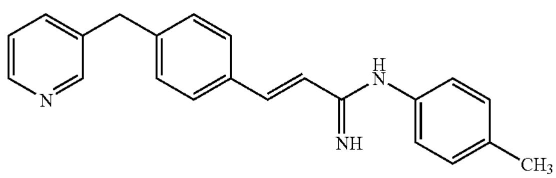 | C | C$_{22}$H$_{21}$N$_3$ | 327.4 | 328.2 |
| 32 | 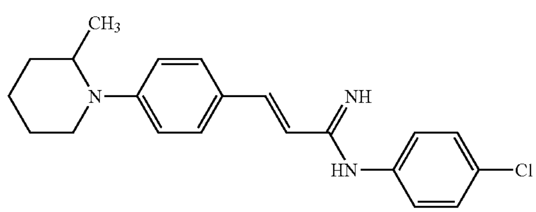 | C | C$_{21}$H$_{24}$ClN$_3$ | 353.9 | 354.1 |
| 33 | 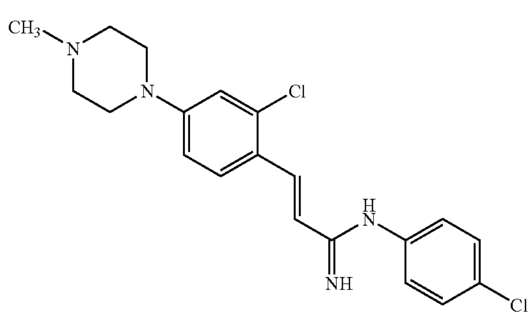 | C | C$_{20}$H$_{22}$Cl$_2$N$_4$ | 389.3 | 389.1, 391.1 |
| 34 | 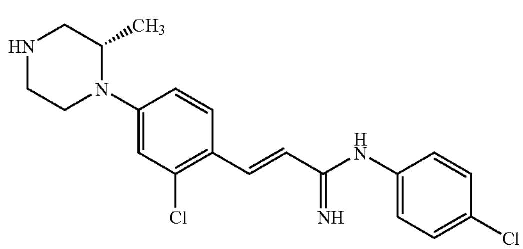 | C, D | C$_{20}$H$_{22}$Cl$_2$N$_4$ | 389.3 | 389.1, 391.1 |

-continued

Table of Synthetic Methods and Analysis of Products:

| Ex | Chemical Structure | Synthetic Method | Formula | Calcd Mass | Obsd mass |
|----|--------------------|------------------|---------|------------|-----------|
| 35 | 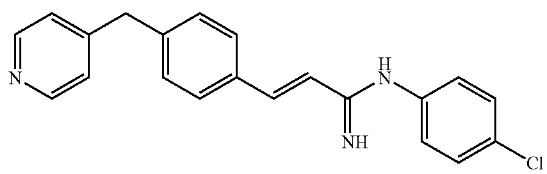 | C | $C_{21}H_{18}ClN_3$ | 347.8 | 348.1 349.1 |
| 36 | 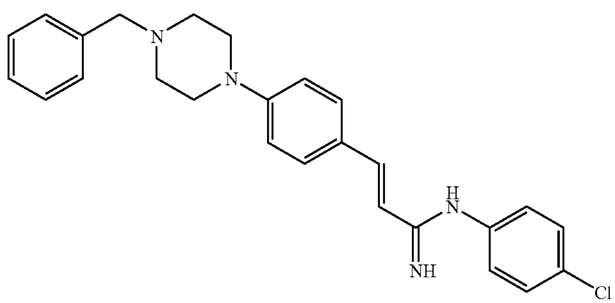 | C | $C_{26}H_{27}ClN_4$ | 431.0 | 431.1 |
| 37 | 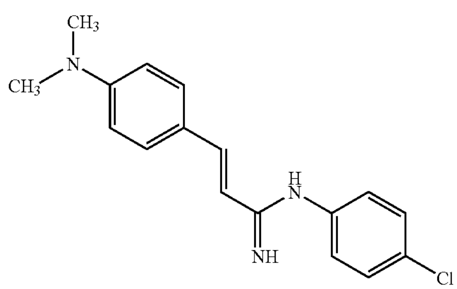 | C | $C_{17}H_{18}ClN_3$ | 299.8 | 300.1 |
| 38 | 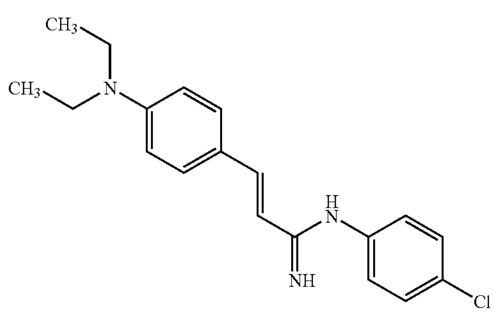 | C | $C_{19}H_{22}ClN_3$ | 327.9 | 328.1 |
| 39 | 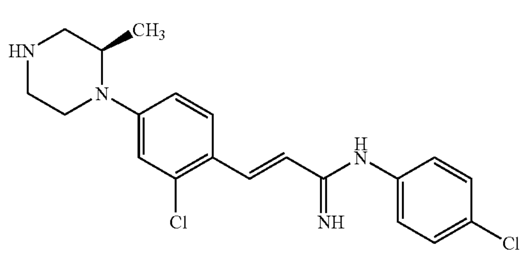 | C, D | $C_{20}H_{22}Cl_2N_4$ | 389.3 | 389.1 391.1 |

-continued

Table of Synthetic Methods and Analysis of Products:

| Ex | Chemical Structure | Synthetic Method | Formula | Calcd Mass | Obsd mass |
|---|---|---|---|---|---|
| 40 | 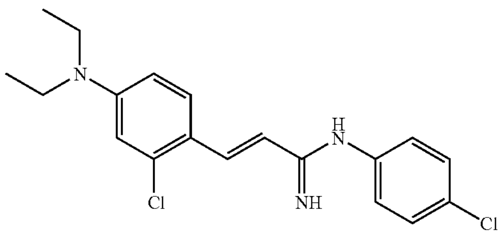 | C | $C_{19}H_{21}Cl_2N_3$ | 362.3 | 362.1 |
| 41 | 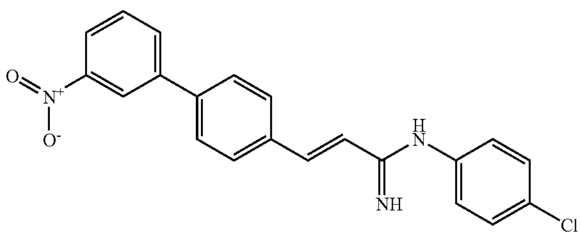 | L | $C_{21}H_{16}ClN_3O_2$ | 377.8 | 378.1 |
| 42 | 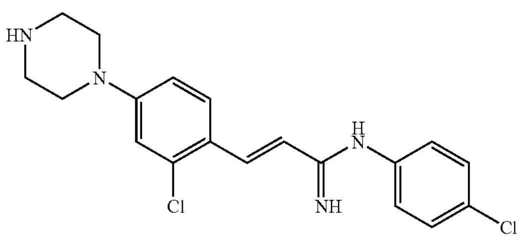 | C, D | $C_{19}H_{20}Cl_2N_4$ | 375.3 | 375.1 |
| 43 | 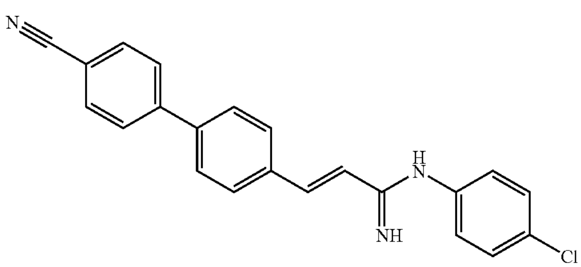 | L | $C_{22}H_{16}ClN_3$ | 357.8 | 358.1 |
| 44 | 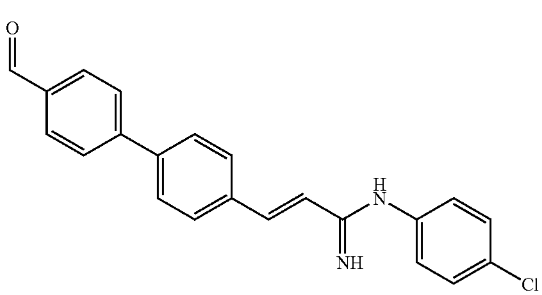 | L | $C_{22}H_{17}ClN_2O$ | 360.8 | 361.1 |
| 45 | 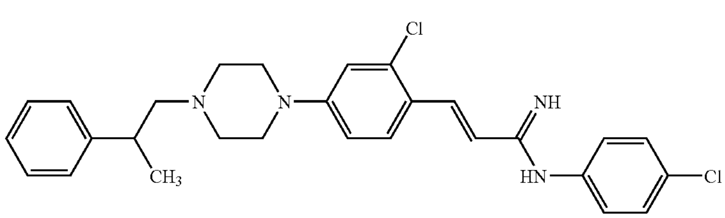 | C, D, E | $C_{28}H_{30}Cl_2N_4$ | 493.5 | 493.1 |

-continued

Table of Synthetic Methods and Analysis of Products:

| Ex | Chemical Structure | Synthetic Method | Formula | Calcd Mass | Obsd mass |
|---|---|---|---|---|---|
| 46 | 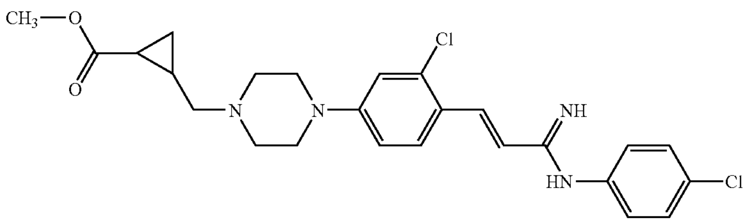 | C, D, E | $C_{25}H_{28}Cl_2N_4O_2$ | 487.4 | 487.1 |
| 47 | 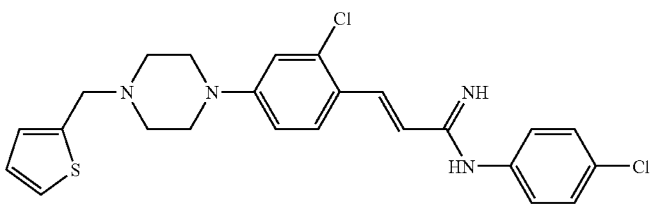 | C, D, E | $C_{24}H_{24}Cl_2N_4S$ | 471.4 | 471.1 |
| 48 | 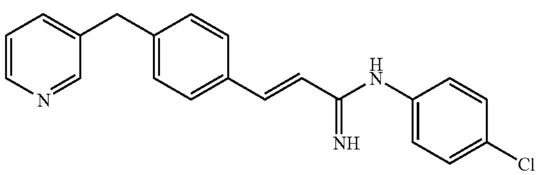 | C | $C_{21}H_{18}ClN_3$ | 347.8 | 348.1 |
| 49 | 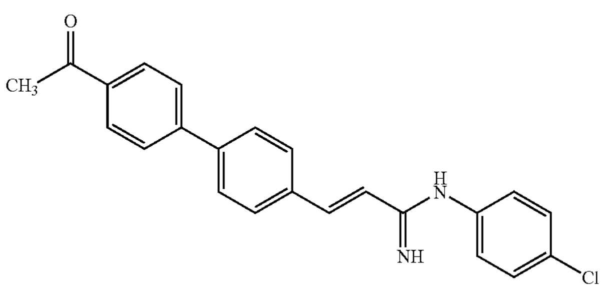 | L | $C_{23}H_{19}ClN_2O$ | 374.9 | 375.1 |
| 50 | 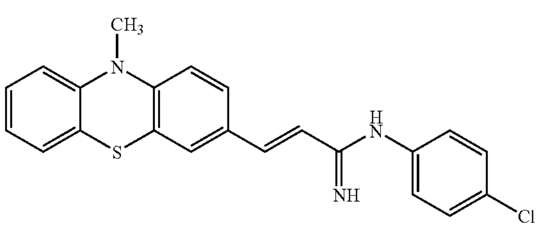 | C | $C_{22}H_{18}ClN_3S$ | 391.9 | 392.1 |
| 51 | 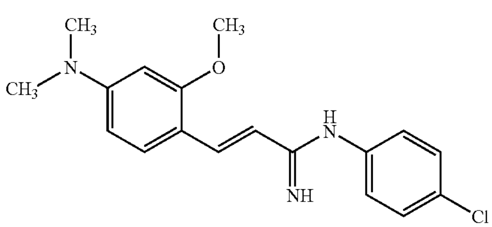 | C | $C_{18}H_{20}ClN_3O$ | 329.8 | 330.1 |

-continued
Table of Synthetic Methods and Analysis of Products:
| Ex | Chemical Structure | Synthetic Method | Formula | Calcd Mass | Obsd mass |
|---|---|---|---|---|---|
| 52 | 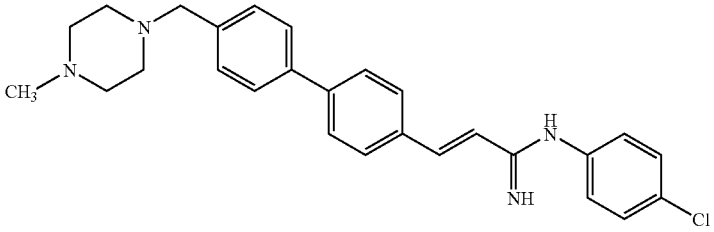 | E | $C_{27}H_{29}ClN_4$ | 445.0 | 445.2 |
| 53 | 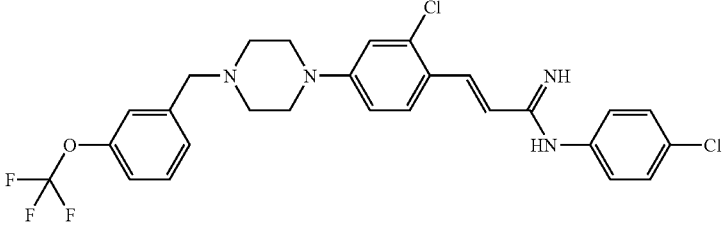 | C, D, E | $C_{27}H_{25}Cl_2F_3N_4O$ | 549.4 | 549.1 |
| 54 | 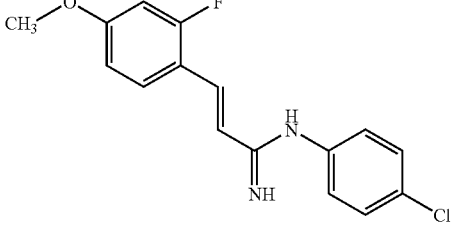 | C | $C_{16}H_{14}ClFN_2O$ | 304.8 | 305.0 |
| 55 | 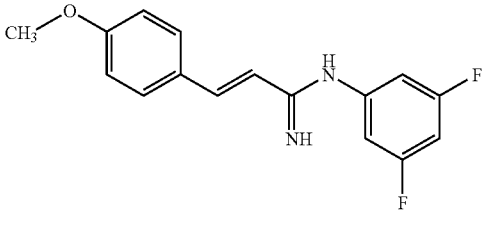 | R | $C_{16}H_{14}F_2N_2O$ | 288.3 | 289.1 |
| 56 | 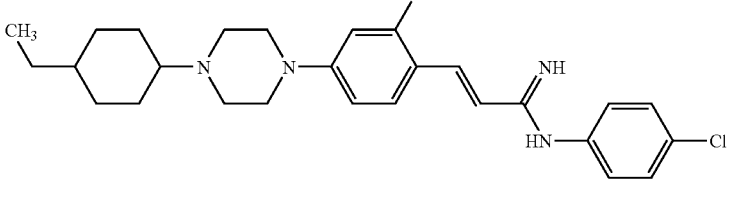 | C, D, E | $C_{27}H_{34}Cl_2N_4$ | 485.5 | 485.1 |
| 57 | 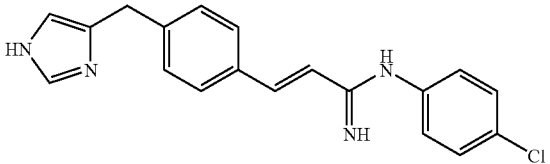 |  | $C_{19}H_{17}ClN_4$ | 336.8 |  |

-continued

Table of Synthetic Methods and Analysis of Products:

| Ex | Chemical Structure | Synthetic Method | Formula | Calcd Mass | Obsd mass |
|---|---|---|---|---|---|
| 58 | 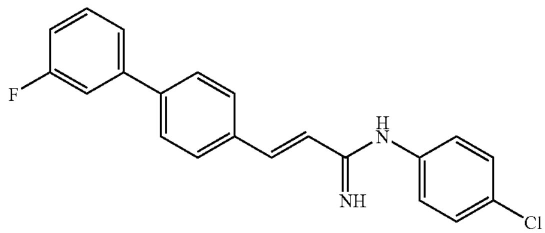 | L | $C_{21}H_{16}ClFN_2$ | 350.8 | 351.1 |
| 59 | 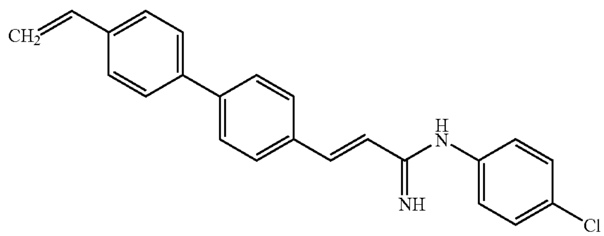 | L | $C_{23}H_{19}ClN_2$ | 358.9 | 359.1 |
| 60 | 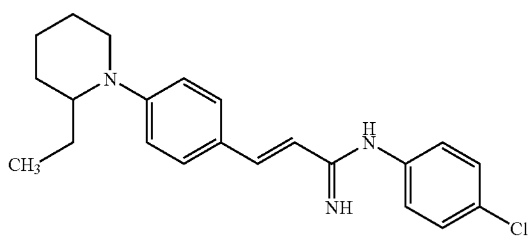 | C | $C_{22}H_{26}ClN_3$ | 367.9 | 368.1 |
| 61 | 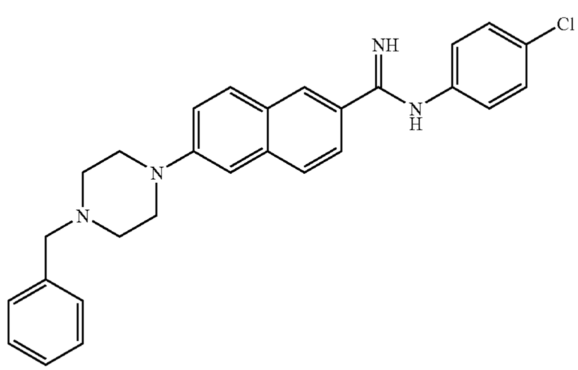 | E | $C_{28}H_{27}ClN_4$ | 455.0 | 455.1 |
| 62 | 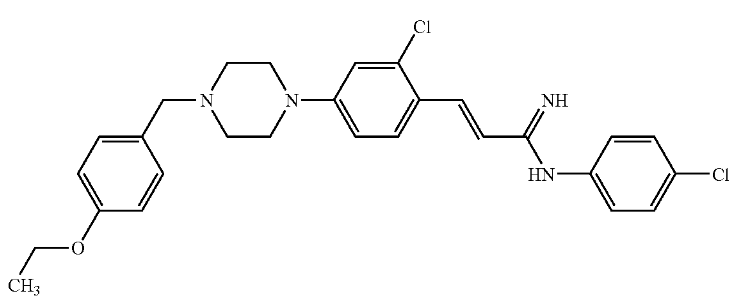 | C, D, E | $C_{28}H_{30}Cl_2N_4O$ | 509.5 | 509.1 |

-continued

Table of Synthetic Methods and Analysis of Products:

| Ex | Chemical Structure | Synthetic Method | Formula | Calcd Mass | Obsd mass |
|---|---|---|---|---|---|
| 63 | 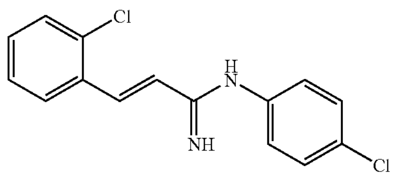 | C, D, E | $C_{26}H_{32}Cl_2N_4$ | 471.5 | 471.1 |
| 64 | 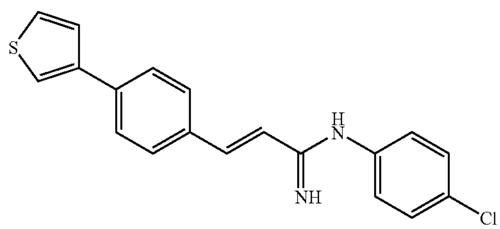 | L | $C_{19}H_{15}ClN_2S$ | 338.9 | 339.1 |
| 65 | 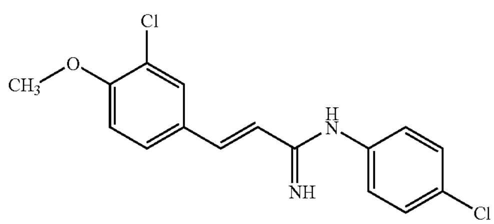 | C | $C_{16}H_{14}Cl_2N_2O$ | 321.2 | 321.1 |
| 66 | 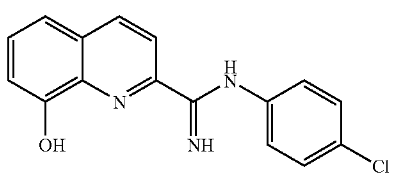 | C | $C_{16}H_{12}ClN_3O$ | 297.7 | 298.1 |
| 67 | 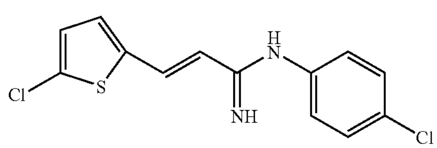 | C | $C_{13}H_{10}Cl_2N_2S$ | 297.2 | 297.1 |
| 68 | 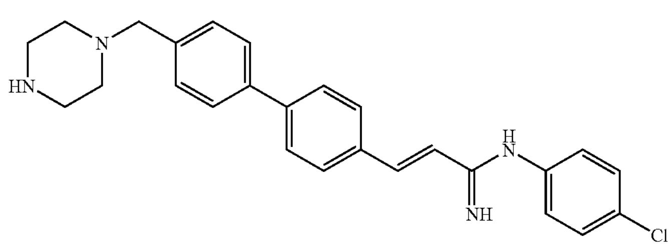 | D | $C_{26}H_{27}ClN_4$ | 431.0 | 431.1 |
| 69 | 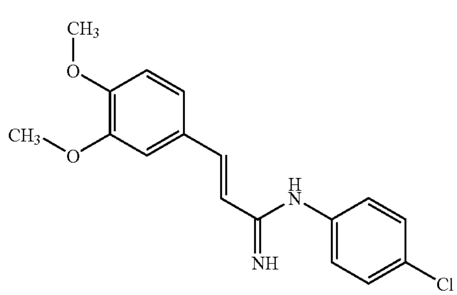 | C | $C_{17}H_{17}ClN_2O_2$ | 316.8 | 317.1 |

-continued

Table of Synthetic Methods and Analysis of Products:

| Ex | Chemical Structure | Synthetic Method | Formula | Calcd Mass | Obsd mass |
|---|---|---|---|---|---|
| 70 | 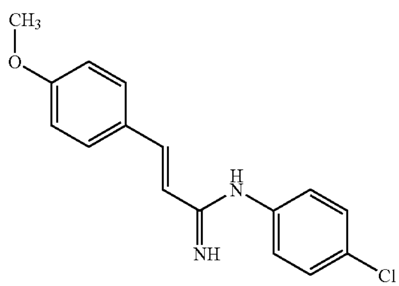 | C | $C_{16}H_{15}ClN_2O$ | 286.8 | 287.1 |
| 71 | 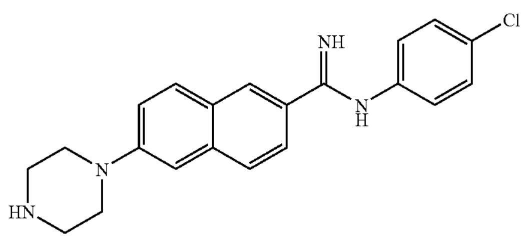 | C | $C_{21}H_{21}ClN_4$ | 364.9 | 365.1 |
| 72 | 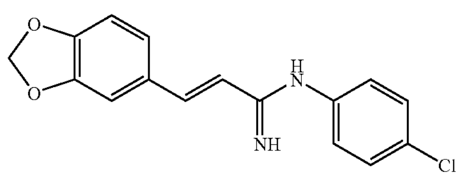 | C | $C_{16}H_{13}ClN_2O_2$ | 300.7 | 301.1 |
| 73 | 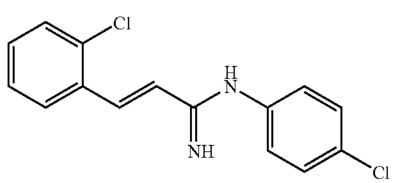 | C | $C_{15}H_{12}Cl_2N_2$ | 291.2 | 291.1 |
| 74 | 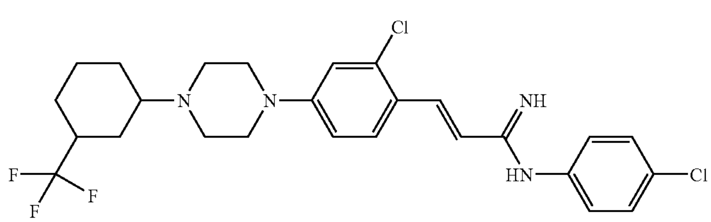 | C, D, E | $C_{26}H_{29}Cl_2F_3N_4$ | 525.4 | 525.1 |
| 75 | 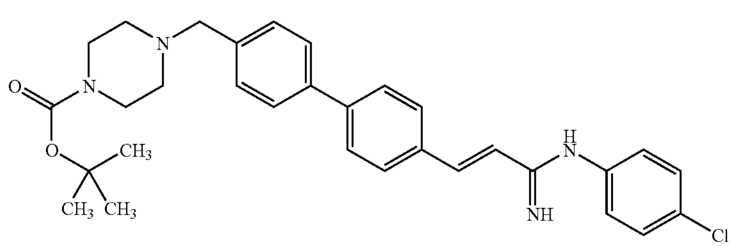 | E | $C_{31}H_{35}ClN_4O_2$ | 531.1 | 531.2 |

-continued

Table of Synthetic Methods and Analysis of Products:

| Ex | Chemical Structure | Synthetic Method | Formula | Calcd Mass | Obsd mass |
|---|---|---|---|---|---|
| 76 | 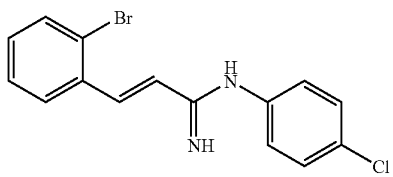 | C | $C_{15}H_{12}BrClN_2$ | 335.6 | 335.1 337.1 |
| 77 | 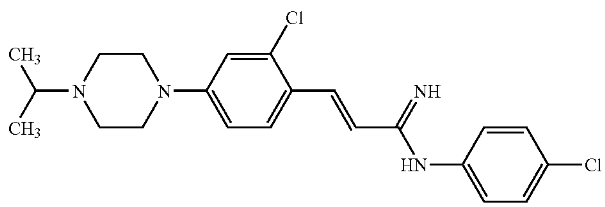 | C, D, E | $C_{22}H_{26}Cl_2N_4$ | 417.4 | 416.6 |
| 78 | 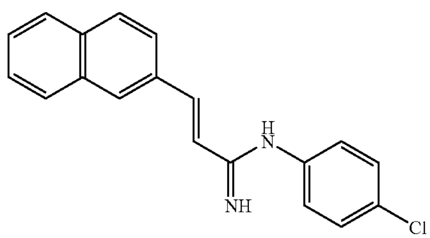 | C | $C_{19}H_{15}ClN_2$ | 306.8 | 307.1 |
| 79 | 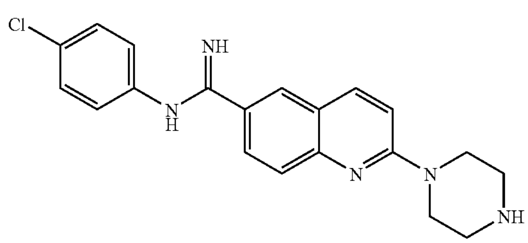 | C | $C_{20}H_{20}ClN_5$ | 365.9 | 366.1 |
| 80 | 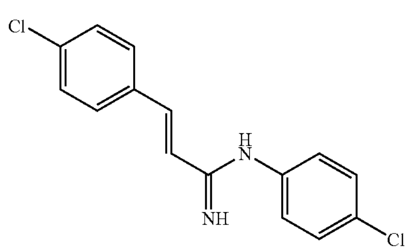 | C | $C_{15}H_{12}Cl_2N_2$ | 291.2 | 291.0 |
| 81 | 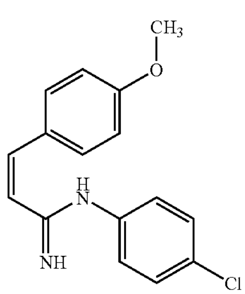 | C | $C_{16}H_{15}ClN_2O$ | 286.8 | 287.1 |

-continued

Table of Synthetic Methods and Analysis of Products:

| Ex | Chemical Structure | Synthetic Method | Formula | Calcd Mass | Obsd mass |
|---|---|---|---|---|---|
| 82 | 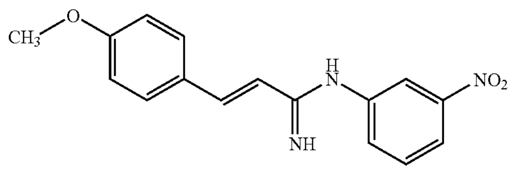 | R | C$_{16}$H$_{15}$N$_3$O$_3$ | 297.3 | 298.1 |
| 83 | 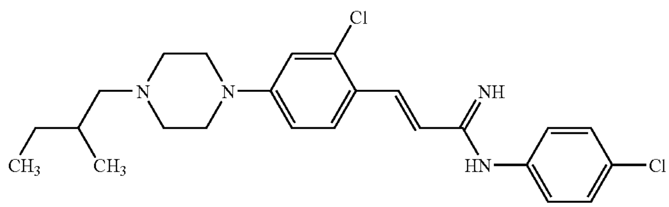 | C, D, E | C$_{24}$H$_{30}$Cl$_2$N$_4$ | 445.4 | 445.3 |
| 84 | 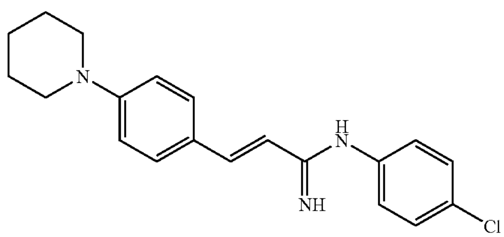 | C | C$_{20}$H$_{22}$ClN$_3$ | 339.9 | 340.1 |
| 85 | 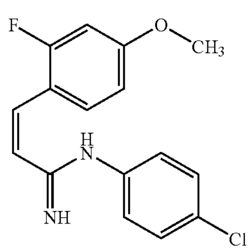 | C | C$_{16}$H$_{14}$ClFN$_2$O | 304.8 | 305.1 |
| 86 | 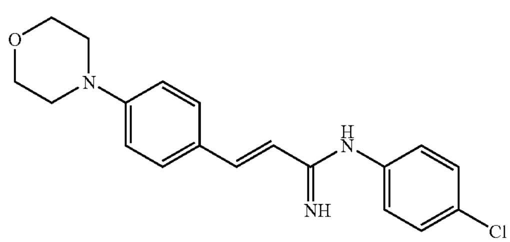 | C | C$_{19}$H$_{20}$ClN$_3$O | 341.8 | 342.1 |
| 87 | 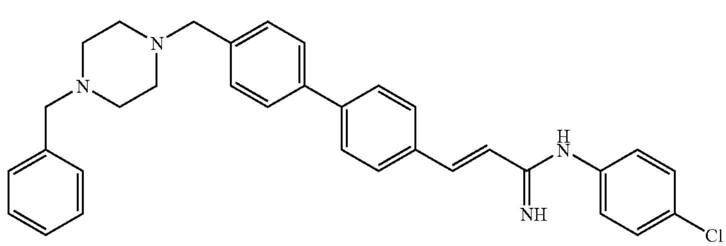 | E | C$_{33}$H$_{33}$ClN$_4$ | 521.1 | 521.1 |

-continued

Table of Synthetic Methods and Analysis of Products:

| Ex | Chemical Structure | Synthetic Method | Formula | Calcd Mass | Obsd mass |
|---|---|---|---|---|---|
| 88 | 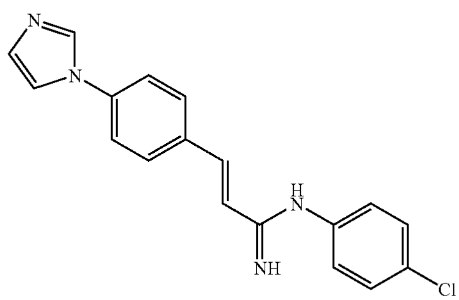 | C | $C_{18}H_{15}ClN_4$ | 322.8 | 323.1 |
| 89 | 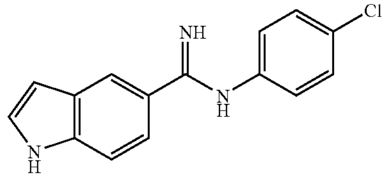 | C | $C_{15}H_{12}ClN_3$ | 269.7 | 270.0 |
| 90 | 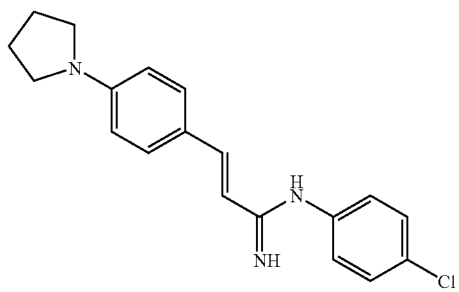 | C | $C_{19}H_{20}ClN_3$ | 325.8 | 326.1 |
| 91 | 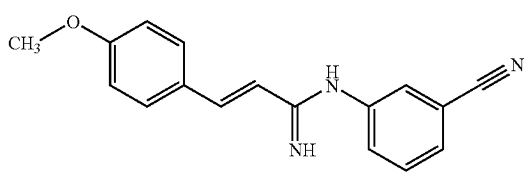 | R | $C_{17}H_{15}N_3O$ | 277.3 | 278.1 |
| 92 | 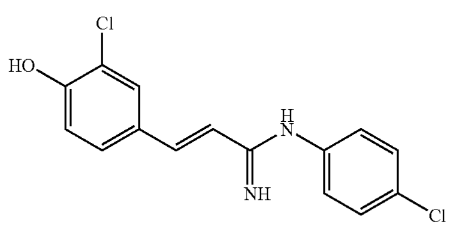 | N | $C_{15}H_{12}Cl_2N_2O$ | 307.2 | 307.1 |
| 93 | 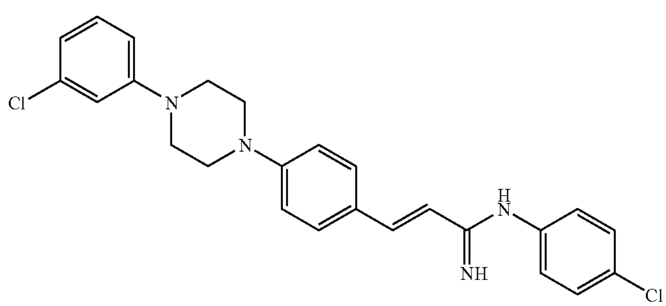 | C | $C_{25}H_{24}Cl_2N_4$ | 451.4 | 451.1 453.1 |

-continued

Table of Synthetic Methods and Analysis of Products:

| Ex | Chemical Structure | Synthetic Method | Formula | Calcd Mass | Obsd mass |
|---|---|---|---|---|---|
| 94 | 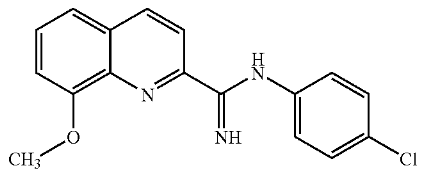 | O | $C_{17}H_{14}ClN_3O$ | 311.8 | 312.1 |
| 95 | 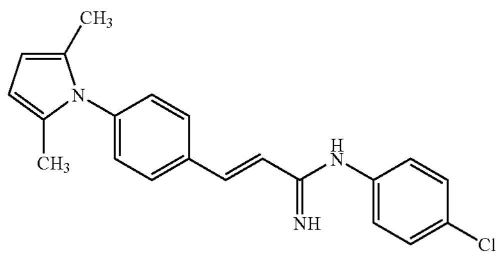 | C | $C_{21}H_{20}ClN_3$ | 349.9 | 350.6 |
| 96 | 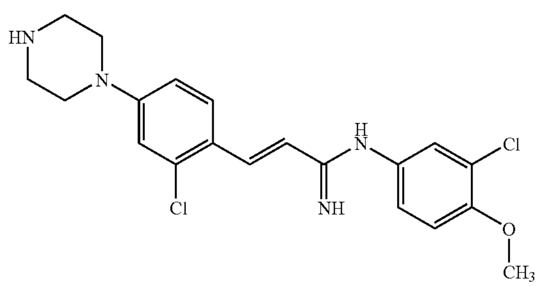 | C | $C_{20}H_{22}Cl_2N_4O$ | 405.3 | 405.1 |
| 97 | 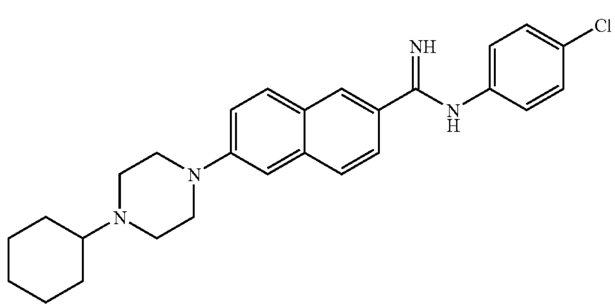 | C | $C_{27}H_{31}ClN_4$ | 447.0 | 447.1 |
| 98 | 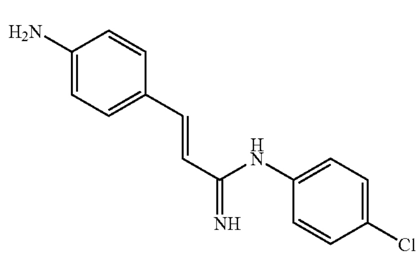 | C + SnCl$_2$, EtOH | $C_{15}H_{14}ClN_3$ | 271.7 | 272.1 |

-continued

Table of Synthetic Methods and Analysis of Products:

| Ex | Chemical Structure | Synthetic Method | Formula | Calcd Mass | Obsd mass |
|---|---|---|---|---|---|
| 99 | 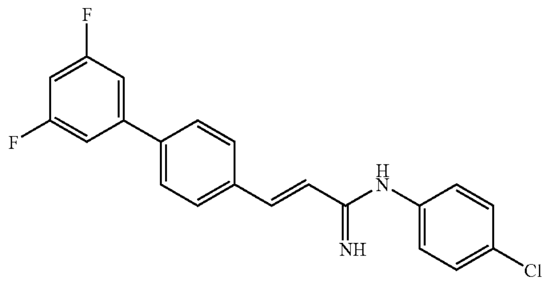 | L | $C_{21}H_{15}ClF_2N_2$ | 368.8 | 369.1 |
| 100 | 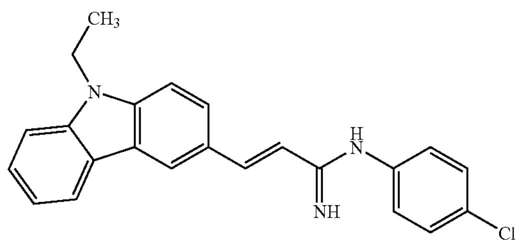 | C | $C_{23}H_{20}ClN_3$ | 373.9 | 374.1 |
| 101 | 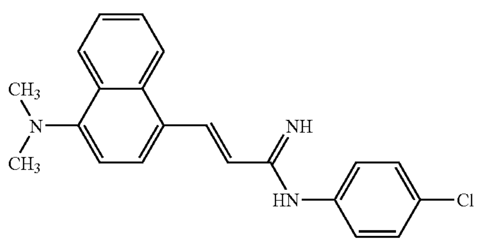 | C | $C_{21}H_{20}ClN_3$ | 349.9 | 349.8 |
| 102 | 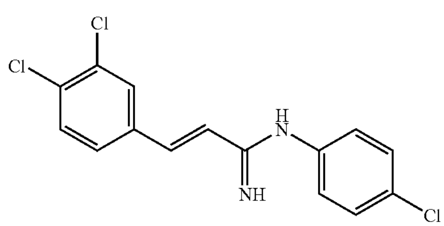 | C | $C_{15}H_{11}Cl_3N_2$ | 325.6 | 325.1 |
| 103 | 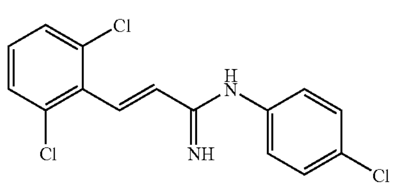 | C | $C_{15}H_{11}Cl_3N_2$ | 325.6 | 327.1 |
| 104 | 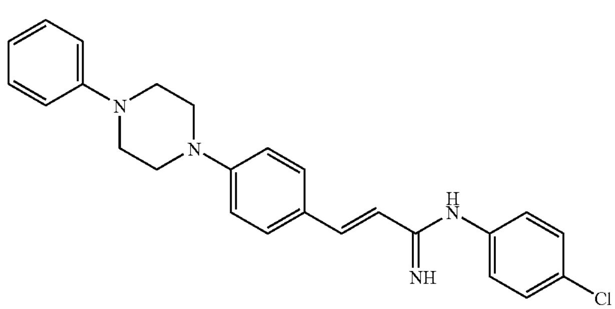 | C | $C_{25}H_{25}ClN_4$ | 417.0 | 417.1 |

-continued

Table of Synthetic Methods and Analysis of Products:

| Ex | Chemical Structure | Synthetic Method | Formula | Calcd Mass | Obsd mass |
|---|---|---|---|---|---|
| 105 | 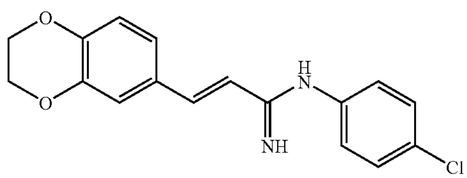 | C | $C_{17}H_{15}ClN_2O_2$ | 314.8 | 315.1 |
| 106 | 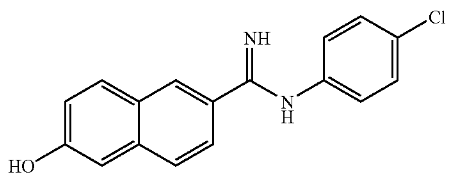 | N | $C_{17}H_{13}ClN_2O$ | 296.8 | 297.1 |
| 107 | 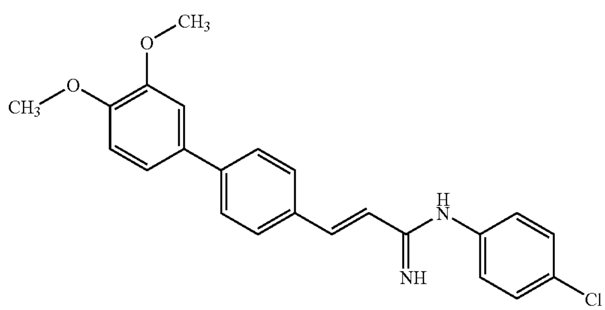 | L | $C_{23}H_{21}ClN_2O_2$ | 392.9 | 393.1 |
| 108 | 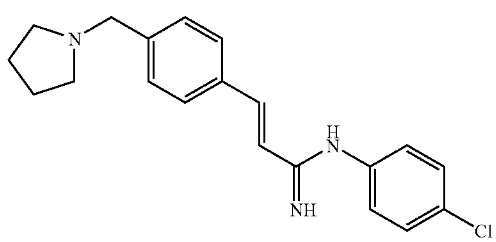 | C | $C_{20}H_{22}ClN_3$ | 339.9 | 340.1 |
| 109 | 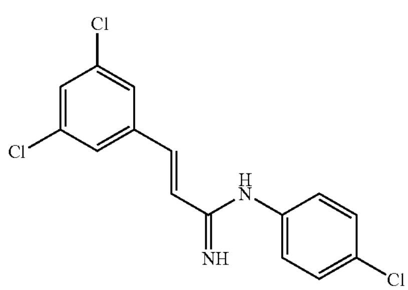 | C | $C_{15}H_{11}Cl_3N_2$ | 325.6 | 325.0 327.1 |
| 110 | 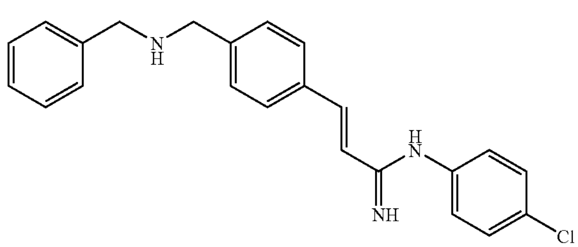 | C | $C_{23}H_{22}ClN_3$ | 375.9 | 376.1 |

-continued
Table of Synthetic Methods and Analysis of Products:
| Ex | Chemical Structure | Synthetic Method | Formula | Calcd Mass | Obsd mass |
|---|---|---|---|---|---|
| 111 | 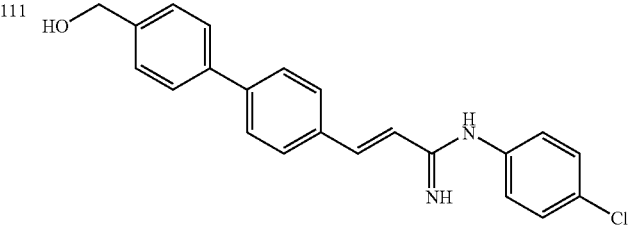 | L | $C_{22}H_{19}ClN_2O$ | 362.9 | 363.1 |
| 112 | 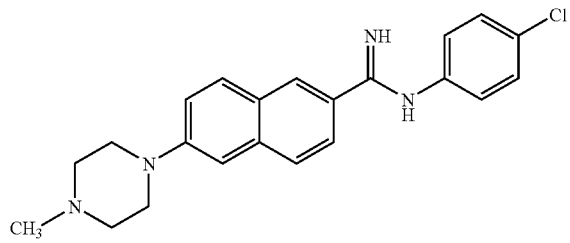 | H | $C_{22}H_{23}ClN_4$ | 378.9 | 379.1 |
| 113 | 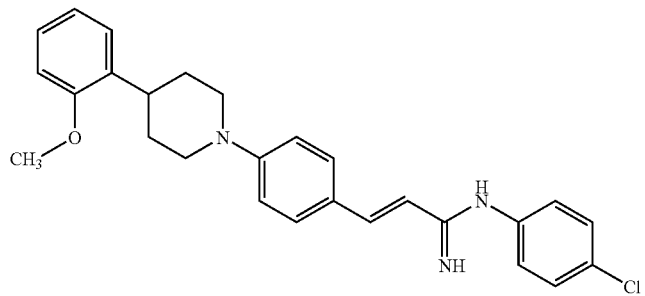 | C | $C_{27}H_{28}ClN_3O$ | 446.0 | 446.1 |
| 114 | 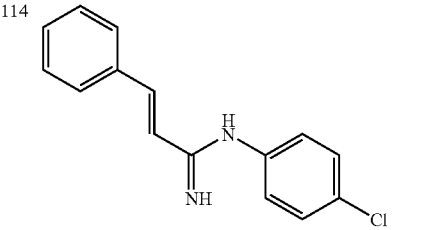 | C | $C_{15}H_{13}ClN_2$ | 256.7 | 257.1 |
| 115 | 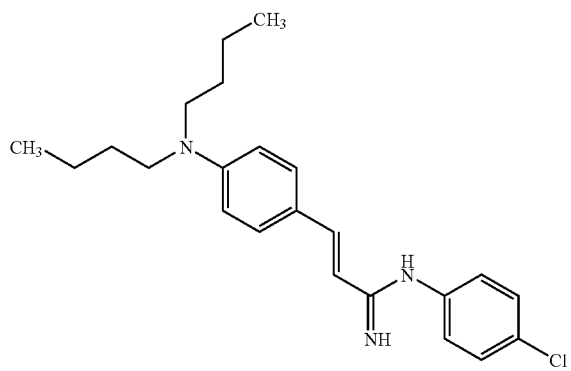 | C | $C_{23}H_{30}ClN_3$ | 384.0 | 384.1 |

-continued

Table of Synthetic Methods and Analysis of Products:

| Ex | Chemical Structure | Synthetic Method | Formula | Calcd Mass | Obsd mass |
|---|---|---|---|---|---|
| 116 | 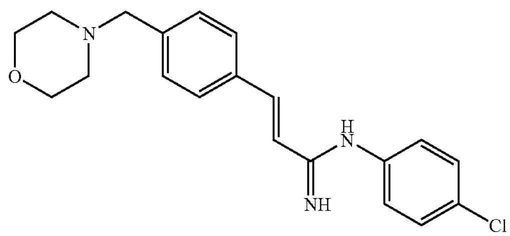 | C | $C_{20}H_{22}ClN_3O$ | 355.9 | 356.1 |
| 117 | 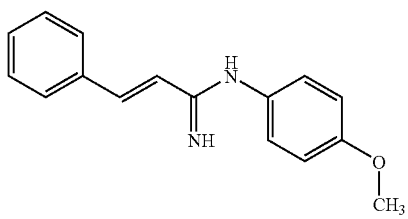 | C | $C_{16}H_{16}N_2O$ | 252.3 | 253.1 |
| 118 | 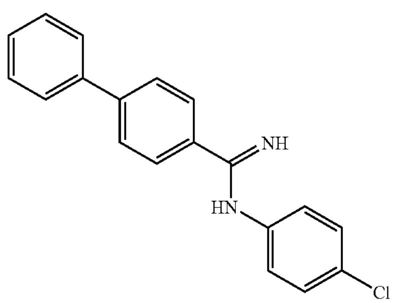 | C | $C_{19}H_{15}ClN_2$ | 306.8 | 307.1 |
| 119 | 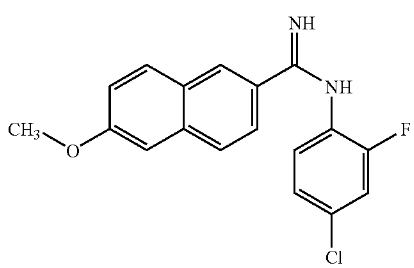 | C | $C_{18}H_{14}ClFN_2O$ | 328.8 | 329.1 |
| 120 | 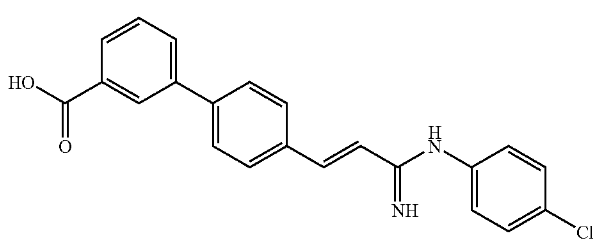 | L | $C_{22}H_{17}ClN_2O_2$ | 376.8 | 377.1 |
| 121 | 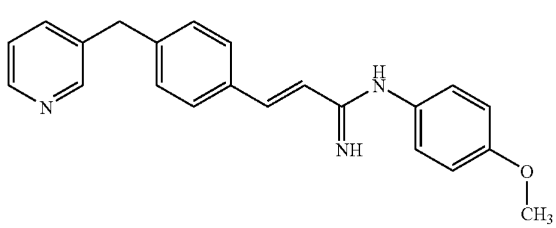 | C | $C_{22}H_{21}N_3O$ | 343.4 | 344.1 |

-continued

Table of Synthetic Methods and Analysis of Products:

| Ex | Chemical Structure | Synthetic Method | Formula | Calcd Mass | Obsd mass |
|---|---|---|---|---|---|
| 122 | 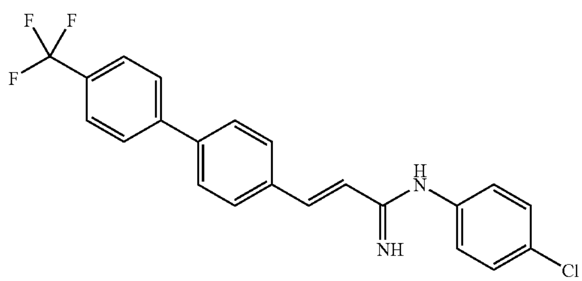 | L | $C_{22}H_{16}ClF_3N_2$ | 400.8 | 401.1 |
| 123 | 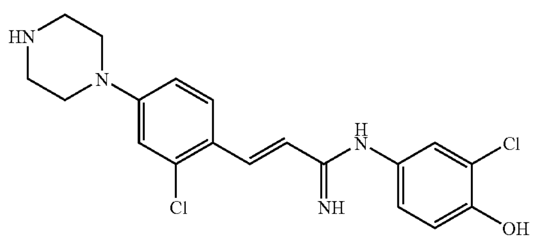 | N | $C_{19}H_{20}Cl_2N_4O$ | 391.3 | 391.1 |
| 124 | 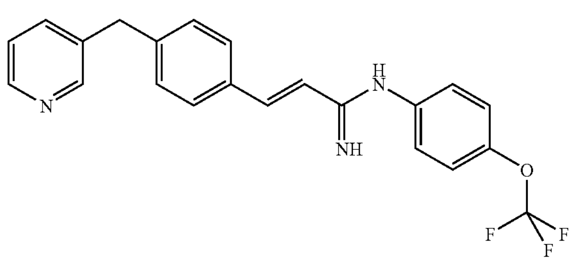 | C | $C_{22}H_{18}F_3N_3O$ | 397.4 | 398.1 |
| 125 | 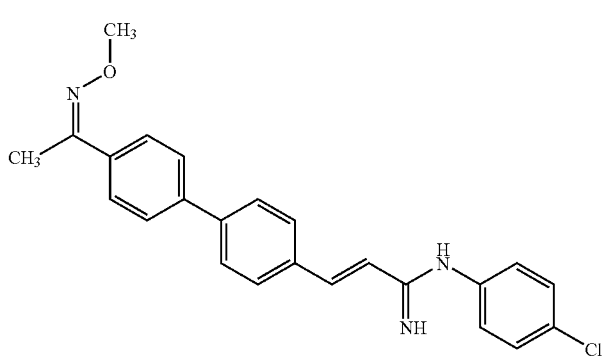 | P | $C_{24}H_{22}ClN_3O$ | 403.9 | 404.1 |
| 126 | 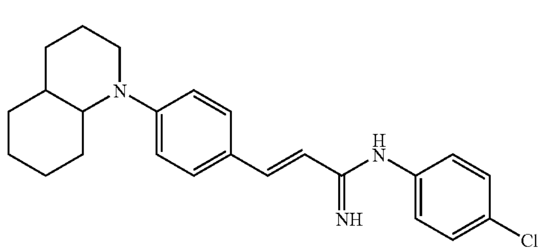 | C | $C_{24}H_{28}ClN_3$ | 394.0 | 394.1 |

-continued

Table of Synthetic Methods and Analysis of Products:

| Ex | Chemical Structure | Synthetic Method | Formula | Calcd Mass | Obsd mass |
|---|---|---|---|---|---|
| 127 | 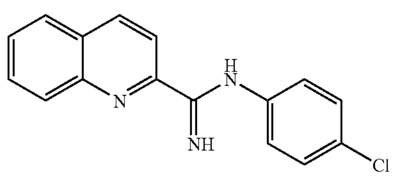 | C | $C_{16}H_{12}ClN_3$ | 281.7 | 282.0 |
| 128 | 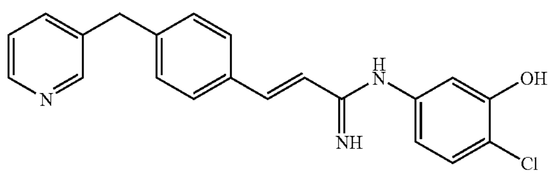 | C + TBAF | $C_{21}H_{18}ClN_3O$ | 363.9 | 364.1 |
| 129 | 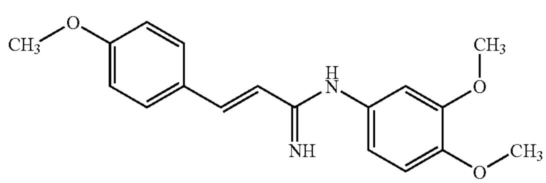 | R | $C_{18}H_{20}N_2O_3$ | 312.4 | 313.1 |
| 130 | 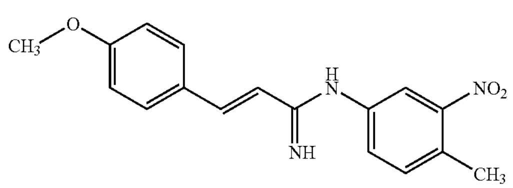 | R | $C_{17}H_{17}N_3O_3$ | 311.3 | 312.1 |
| 131 | 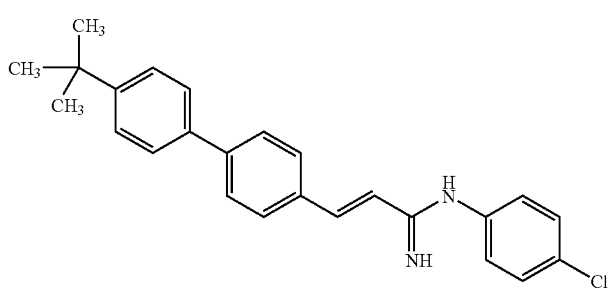 | L | $C_{25}H_{25}ClN_2$ | 389.0 | 390.1 |
| 132 | 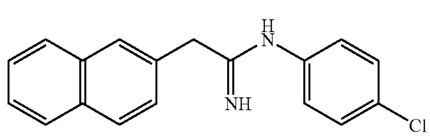 | C | $C_{18}H_{15}ClN_2$ | 294.8 | 295.1 |
| 133 | 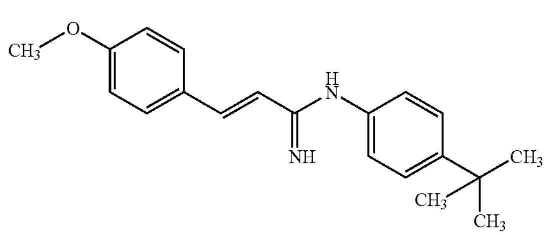 | R | $C_{20}H_{24}N_2O$ | 308.4 | 309.1 |

-continued

Table of Synthetic Methods and Analysis of Products:

| Ex | Chemical Structure | Synthetic Method | Formula | Calcd Mass | Obsd mass |
|---|---|---|---|---|---|
| 134 | ![structure] | | $C_{19}H_{19}ClN_4$ | 338.8 | 339.1 |

The compounds of the present invention exhibit $D_1$ receptor antagonizing activity, which has been correlated with pharmaceutical activity for treating CNS disorders such as OCD, trichotillomania, metabolic disorders such as obesity, eating disorders such as hyperphagia, and diabetes. This utility is manifested by activity in the following assay.

Assay

Biological Activity: Compounds from this disclosure have been biologically characterized by their ability to displace a known $D_1$-like selective ligand, [3H]SCH 23390 from the human Dopamine $D_1$ receptor, and a known D2-like selective ligand, [3H] Methylspiperone, from the human Dopamine D2 and D4 receptors. Selectivity versus other receptors has been demonstrated by comparison of the $D_1$ Ki's with D2, D4, and D5 Ki's.

Affinity values (Ki) of compounds at human dopamine receptors were ascertained using radioligand binding competition assays. Cells expressing $D_1$ (Ltk-cells), $D_2$ (long variant, Ltk-cells), D4 (CHO cells) and D5 (GH4C1 cells) receptors were lysed in hypotonic buffer for membrane preparation. Membranes were incubated with various concentrations of test compound and 1 nM [3H] SCH 23390 (D1 and D5) and 0.2 nM [3H] Methylspiperone for ($D_2$ and $D_4$) assays. Non-specific binding was defined as binding in the presence of 10 micromolar of SCH 23390 for $D_1$ and $D_5$ assays and 10 micromolar butaclamol for $D_2$ and $D_4$ assays. Following incubation to equilibrium (1 hour at room temperature), bound radioligand was separated from free by rapid filtration. Bound radioactivity on the dried filters was quantified by liquid scintillation counting.

Results of the binding assay on compounds of the invention showed Ki ($D_1$) values of 0.9 to 10000 nM and Ki ($D_2$) values of 45 to >50000 nM.

Selectivity is determined by dividing Ki for D2, D4 or D5 receptors by Ki for D1 receptor.

Compounds with Ki ($D_1$) values less than 10000 nM but greater than 50 nM are designated in the table below as D class compounds.

Compounds with Ki ($D_1$) values less than 50 nM but greater than 10 nM are designated in the table below as C class compounds.

Compounds of Ki ($D_1$) values less than 10 nM and a selectivity value greater than 100 are designated in the table below as B class compounds.

Preferred Compounds of the invention have Ki ($D_1$) values less than 5 nM and a selectivity value greater than 500 and are designated by the letter A in the table below.

A preferred embodiment of the claimed compounds is example 42 with a Ki ($D_1$) value of 0.9 and $D_2$:$D_1$ ratio value of 1258.5.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

| Example | Chemical Structure | $D_1$ binding and $D_2$:$D_1$ Selectivity |
|---|---|---|
| 1 | 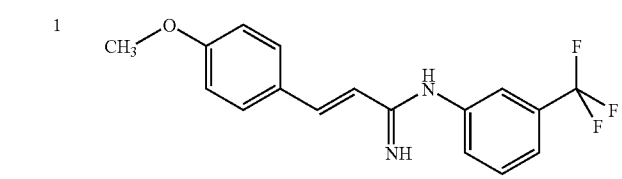 | D |

-continued

| Example | Chemical Structure | $D_1$ binding and $D_2:D_1$ Selectivity |
|---|---|---|
| 2 | 3,5-bis(trifluoromethyl)phenyl-CH=CH-C(=NH)-NH-(4-chlorophenyl) | D |
| 3 | 4-chloro-3-nitrophenyl-CH=CH-C(=NH)-NH-(4-chlorophenyl) | D |
| 4 | 4-(trifluoromethoxy)phenyl-CH=CH-C(=NH)-NH-(4-chlorophenyl) | D |
| 5 | 2-iodophenyl-CH=CH-C(=NH)-NH-(4-chlorophenyl) | D |
| 6 | 4-(piperidin-1-ylmethyl)phenyl-CH=CH-C(=NH)-NH-(4-chlorophenyl) | D |
| 7 | 4-tert-butylphenyl-CH=CH-C(=NH)-NH-(4-chlorophenyl) | C |
| 8 | 4-(pyridin-3-ylmethyl)phenyl-CH=CH-C(=NH)-NH-(4-hydroxyphenyl) | D |

-continued

| Example | Chemical Structure | $D_1$ binding and $D_2:D_1$ Selectivity |
|---|---|---|
| 9 | 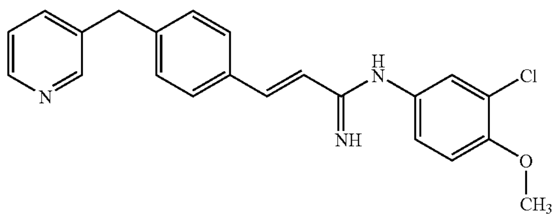 | D |
| 10 | 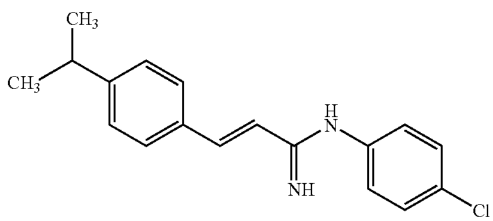 | C |
| 11 | 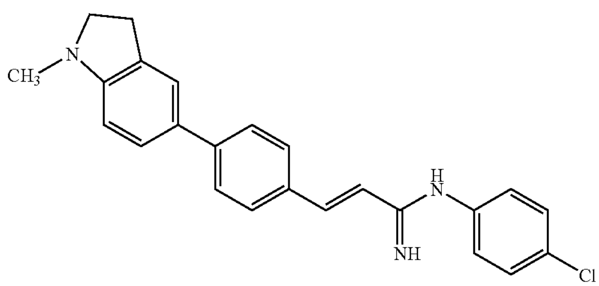 | C |
| 12 | 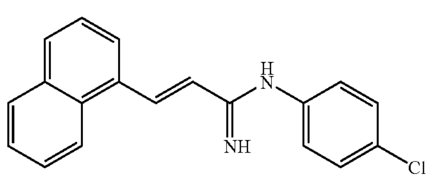 | D |
| 13 | 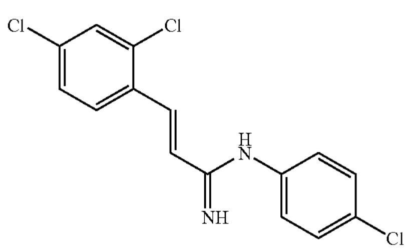 | C |
| 14 | 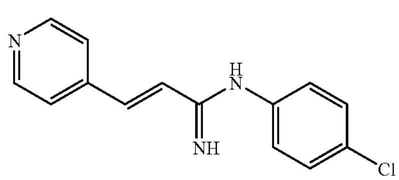 | D |
| 15 | 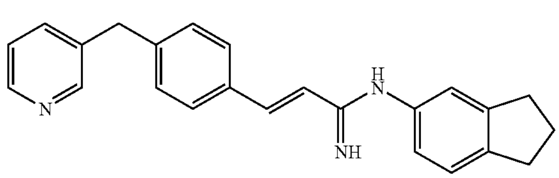 | C |

| Example | Chemical Structure | D₁ binding and D₂:D₁ Selectivity |
|---|---|---|
| 16 | 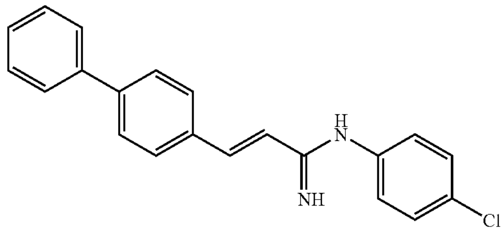 | C |
| 17 | 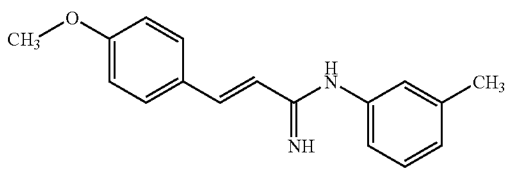 | D |
| 18 | 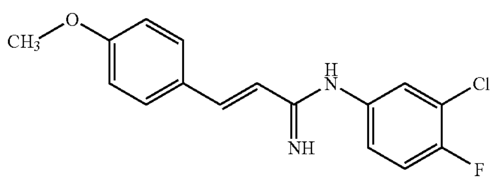 | D |
| 19 | 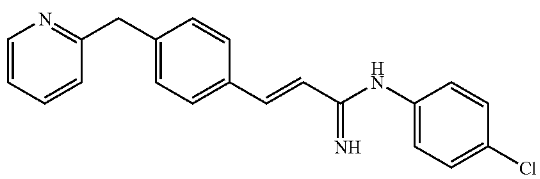 | D |
| 20 | 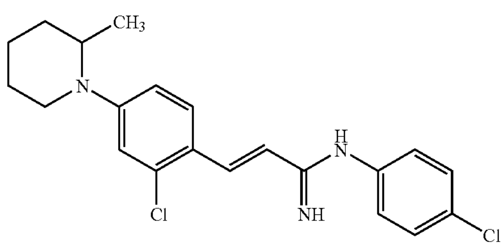 | B |
| 21 | 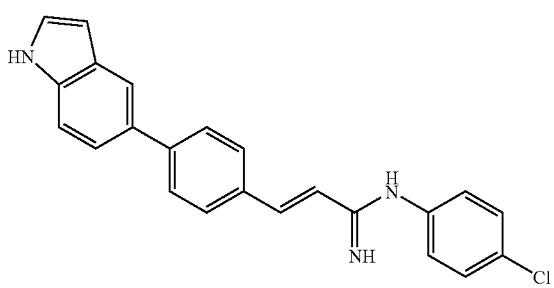 | B |
| 22 | 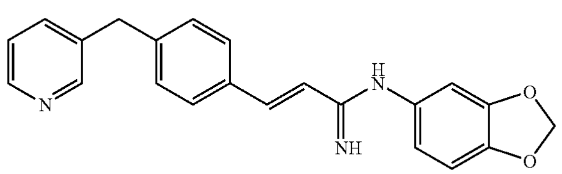 | D |

-continued
| Example | Chemical Structure | D$_1$ binding and D$_2$:D$_1$ Selectivity |
|---|---|---|
| 23 | 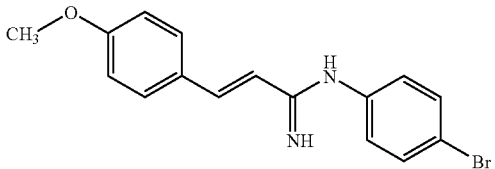 | C |
| 24 | 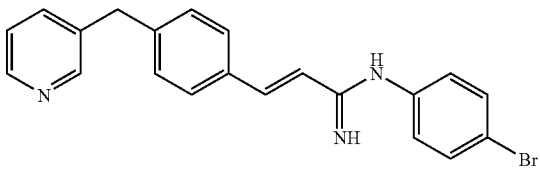 | C |
| 25 | 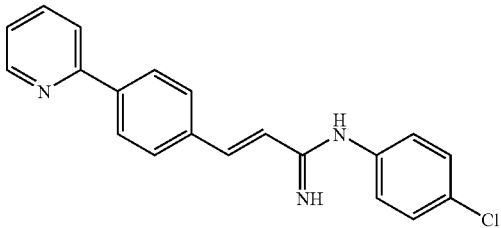 | C |
| 26 | 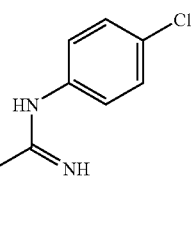 | D |
| 27 | 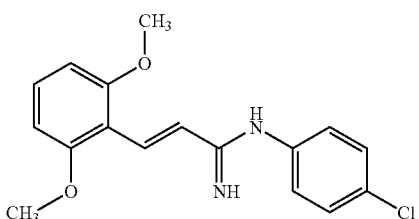 | D |
| 28 | 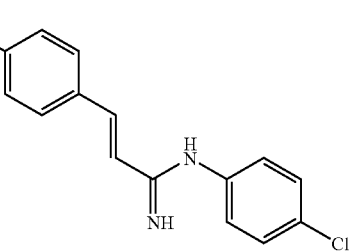 | D |

| Example | Chemical Structure | D₁ binding and D₂:D₁ Selectivity |
|---|---|---|
| 29 | 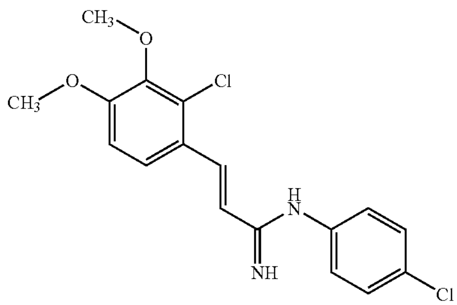 | C |
| 30 | 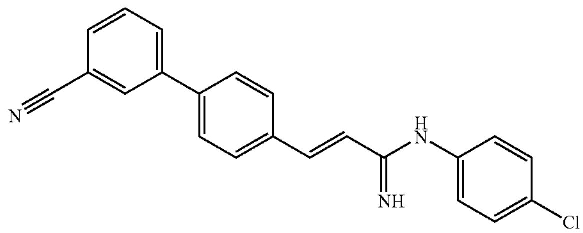 | C |
| 31 | 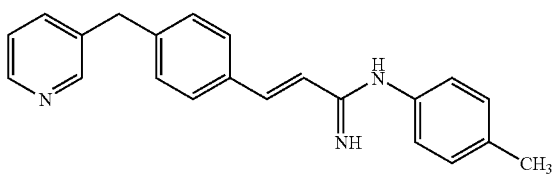 | C |
| 32 | 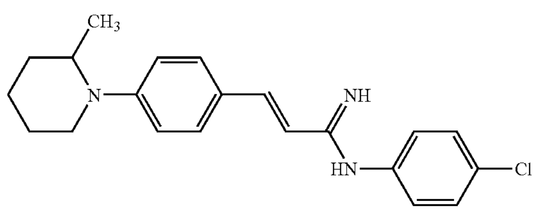 | B |
| 33 | 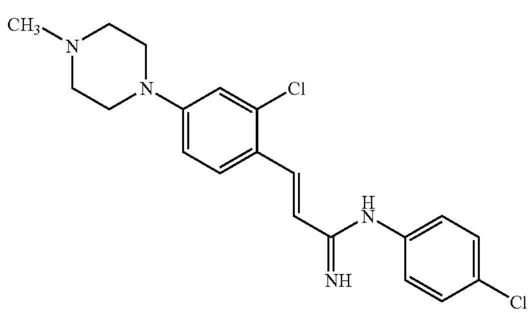 | B |
| 34 | 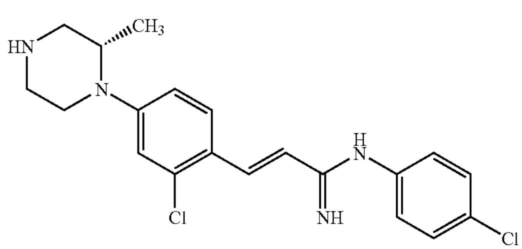 | A |

-continued

| Example | Chemical Structure | D₁ binding and D₂:D₁ Selectivity |
|---------|-------------------|-----------------------------------|
| 35 | 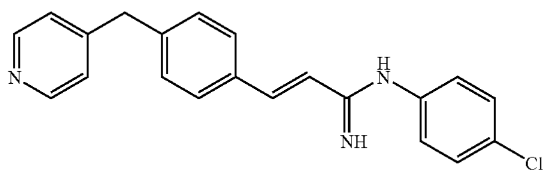 | C |
| 36 | 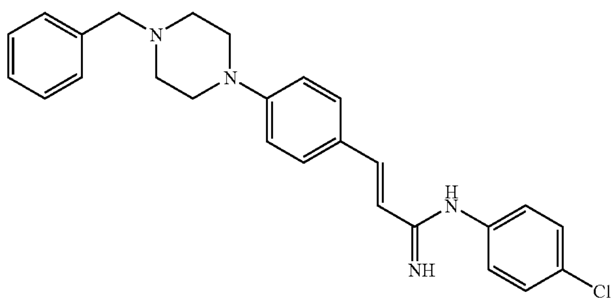 | C |
| 37 | 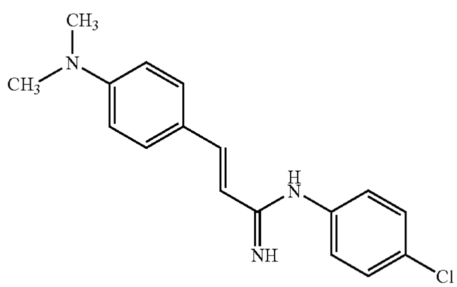 | C |
| 38 | 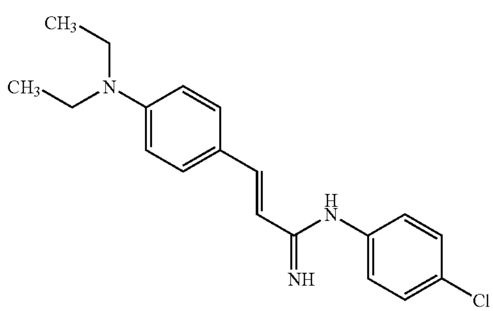 | C |
| 39 | 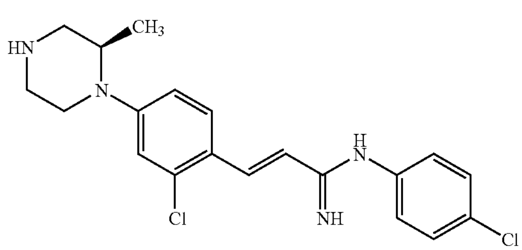 | A |

-continued

| Example | Chemical Structure | $D_1$ binding and $D_2:D_1$ Selectivity |
|---|---|---|
| 40 | 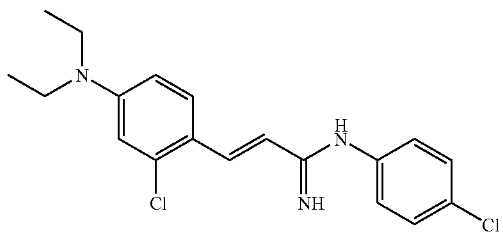 | B |
| 41 | 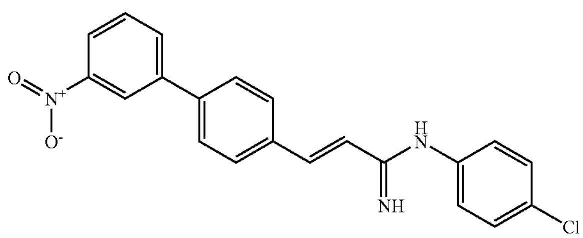 | C |
| 42 | 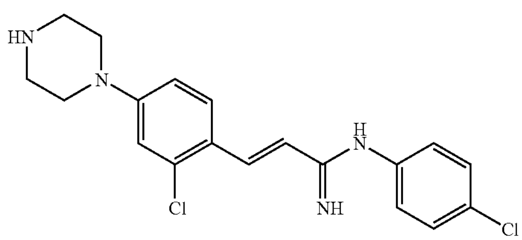 | A |
| 43 | 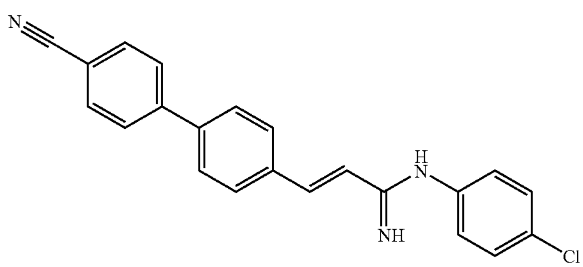 | B |
| 44 | 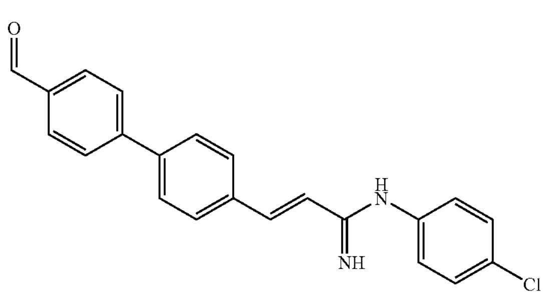 | B |
| 45 | 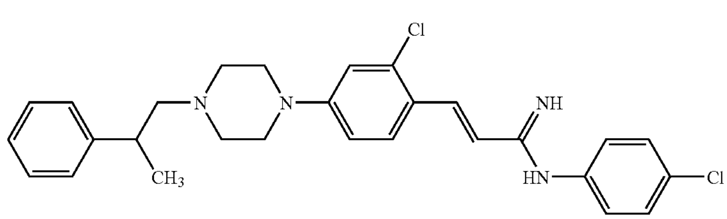 | C |

-continued
| Example | Chemical Structure | D₁ binding and D₂:D₁ Selectivity |
|---|---|---|
| 46 | 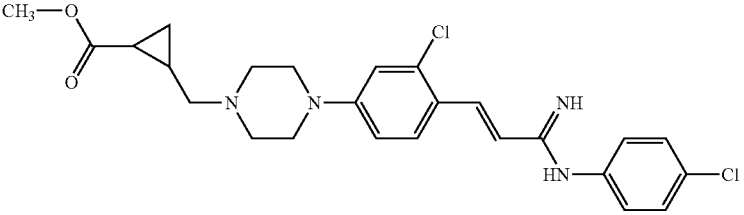 | C |
| 47 | 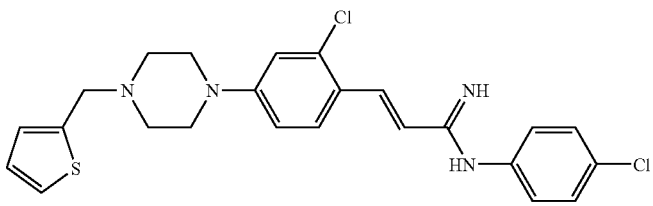 | C |
| 48 | 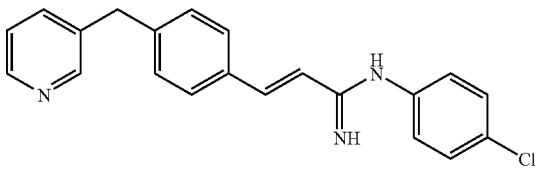 | C |
| 49 | 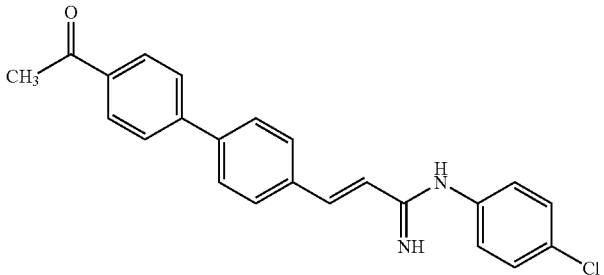 | C |
| 50 | 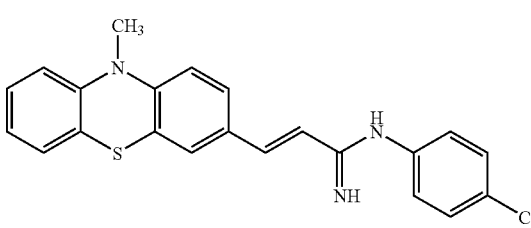 | C |
| 51 | 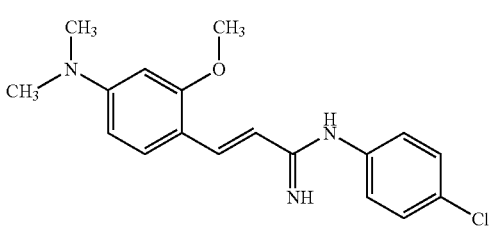 | C |

-continued

| Example | Chemical Structure | D₁ binding and D₂:D₁ Selectivity |
|---|---|---|
| 52 | 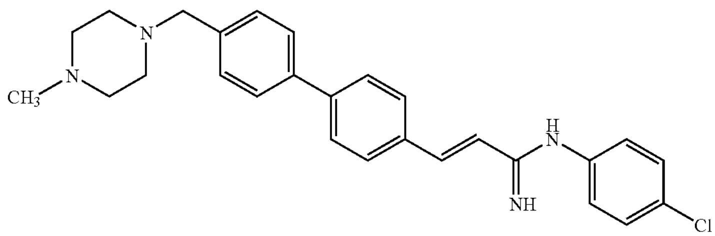 | C |
| 53 | 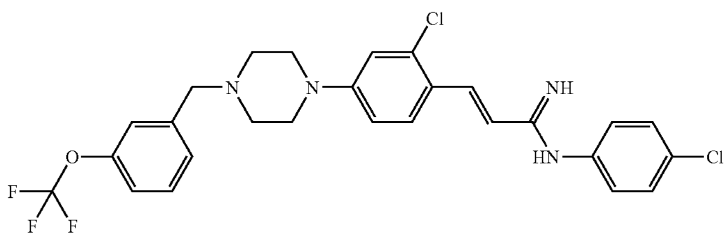 | C |
| 54 | 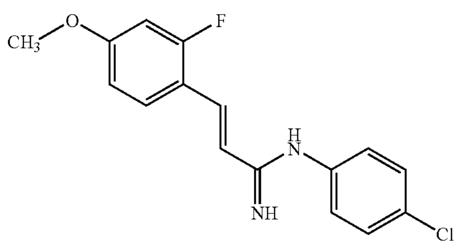 | C |
| 55 | 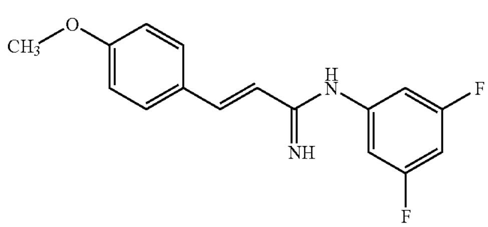 | C |
| 56 | 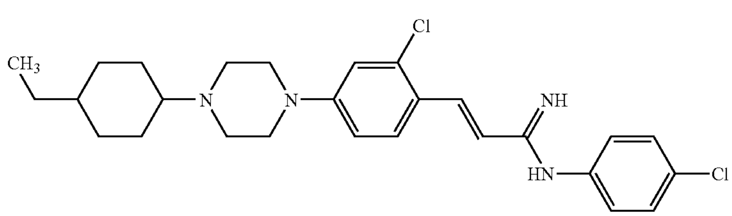 | C |
| 57 | 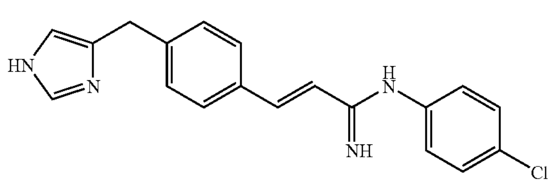 | C |

| Example | Chemical Structure | D₁ binding and D₂:D₁ Selectivity |
|---|---|---|
| 58 | 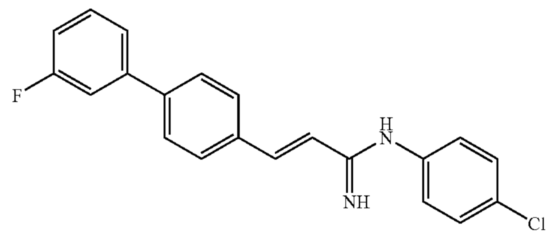 | C |
| 59 | 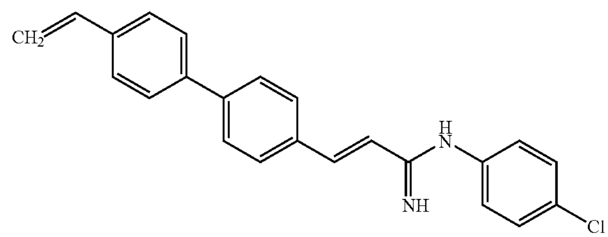 | C |
| 60 | 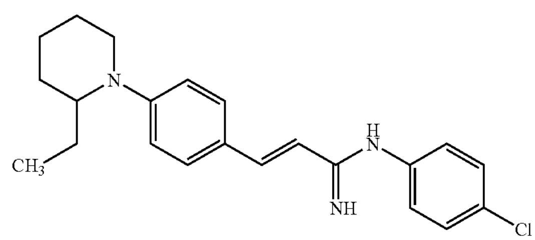 | C |
| 61 | 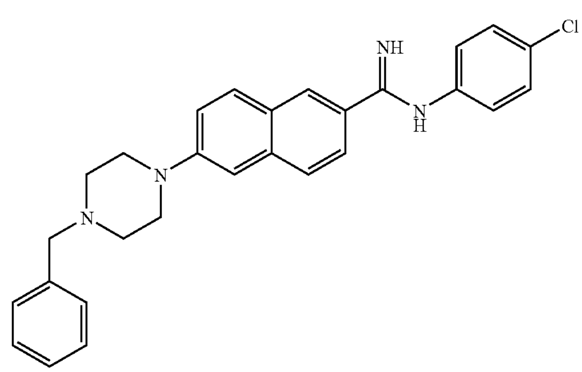 | C |
| 62 | 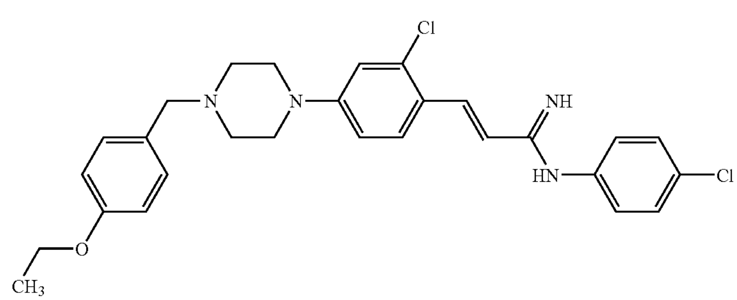 | C |

| Example | Chemical Structure | $D_1$ binding and $D_2:D_1$ Selectivity |
|---|---|---|
| 63 | 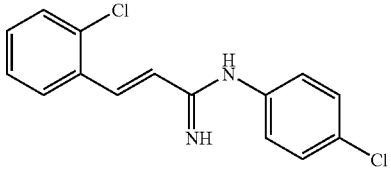 | C |
| 64 | 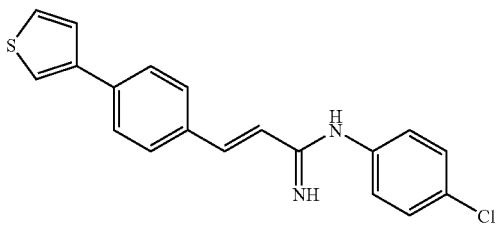 | C |
| 65 | 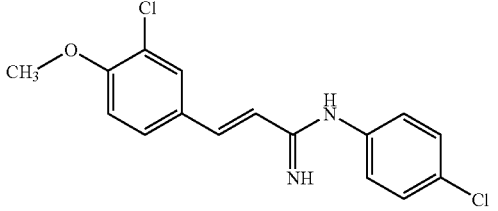 | C |
| 66 | 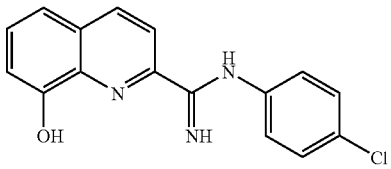 | C |
| 67 | 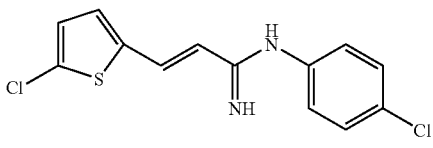 | C |
| 68 | 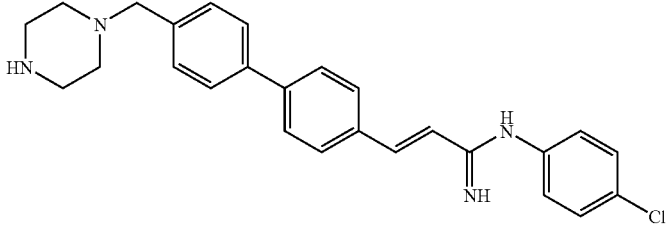 | C |
| 69 | 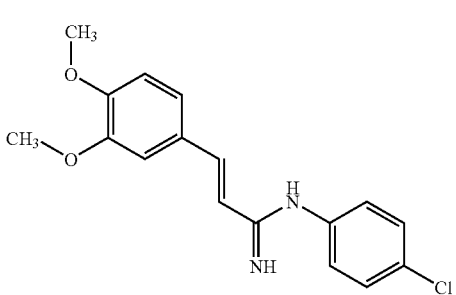 | C |

-continued

| Example | Chemical Structure | D₁ binding and D₂:D₁ Selectivity |
|---------|--------------------|----------------------------------|
| 70 | 4-methoxycinnamamidine N-(4-chlorophenyl) derivative | C |
| 71 | 6-(piperazin-1-yl)naphthalene-2-carboxamidine N-(4-chlorophenyl) derivative | C |
| 72 | 3-(benzo[d][1,3]dioxol-5-yl)acrylamidine N-(4-chlorophenyl) derivative | C |
| 73 | 3-(2-chlorophenyl)acrylamidine N-(4-chlorophenyl) derivative | C |
| 74 | 3-(2-chloro-4-(4-(3-(trifluoromethyl)cyclohexyl)piperazin-1-yl)phenyl)acrylamidine N-(4-chlorophenyl) derivative | C |
| 75 | tert-butyl 4-((4'-(3-((4-chlorophenyl)amino)-3-iminoprop-1-en-1-yl)-[1,1'-biphenyl]-4-yl)methyl)piperazine-1-carboxylate | D |
| 76 | 3-(2-bromophenyl)acrylamidine N-(4-chlorophenyl) derivative | D |

-continued
| Example | Chemical Structure | D$_1$ binding and D$_2$:D$_1$ Selectivity |
|---|---|---|
| 77 | 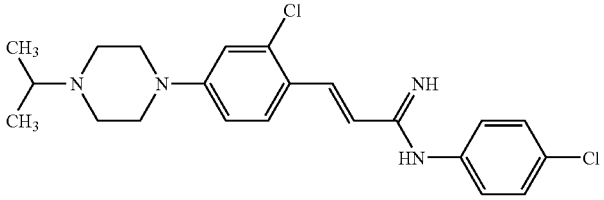 | D |
| 78 | 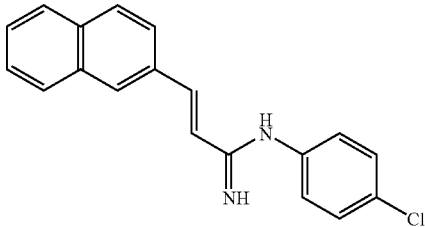 | D |
| 79 | 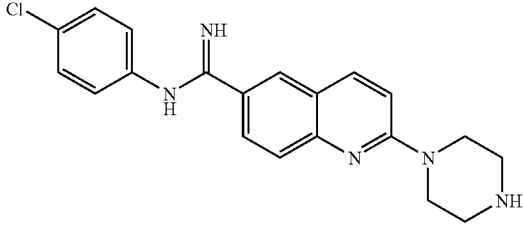 | D |
| 80 | 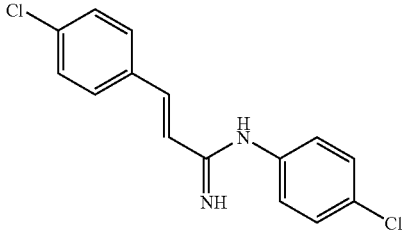 | D |
| 81 | 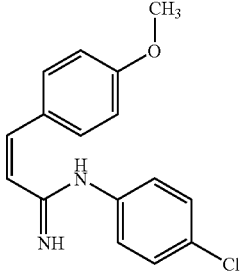 | D |
| 82 | 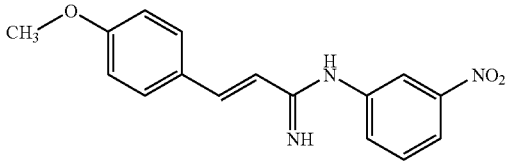 | D |

| Example | Chemical Structure | D₁ binding and D₂:D₁ Selectivity |
|---------|-------------------|----------------------------------|
| 83 | 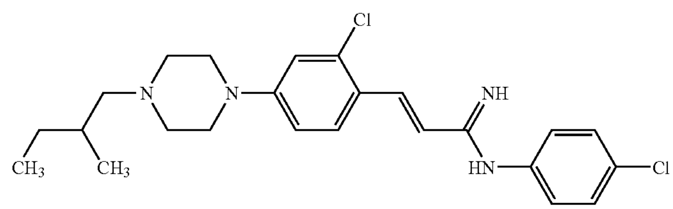 | D |
| 84 | 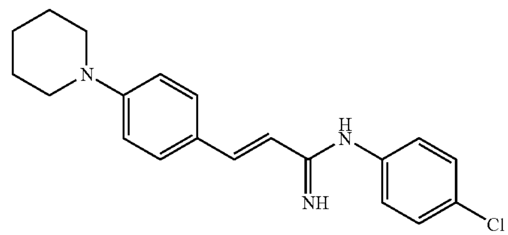 | D |
| 85 | 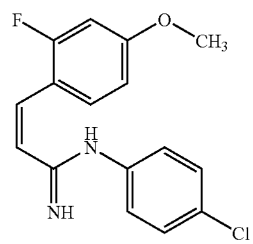 | D |
| 86 | 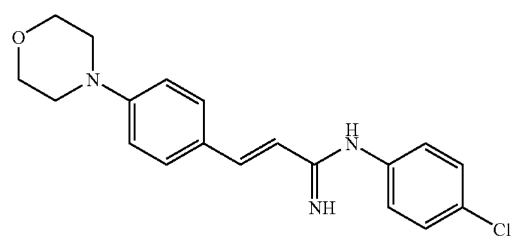 | D |
| 87 | 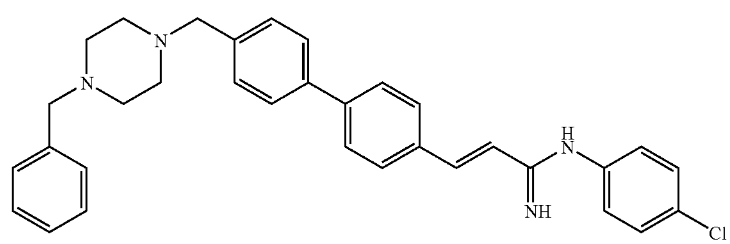 | D |
| 88 | 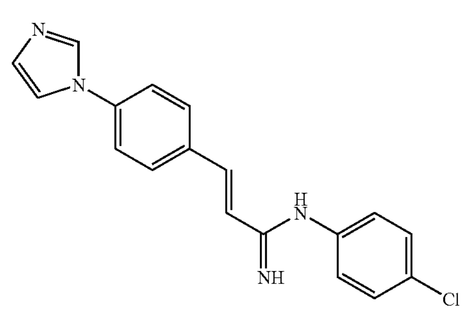 | D |

-continued
| Example | Chemical Structure | D₁ binding and D₂:D₁ Selectivity |
|---|---|---|
| 89 | 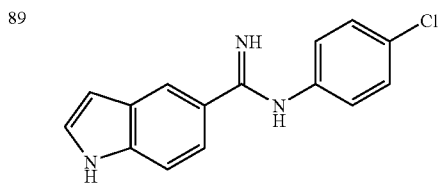 | D |
| 90 | 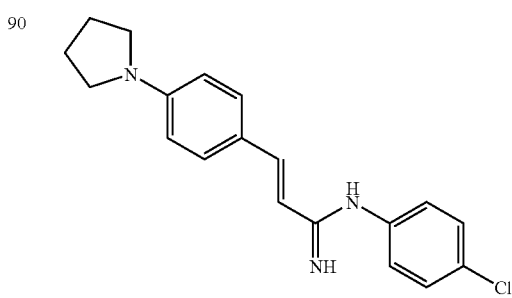 | D |
| 91 | 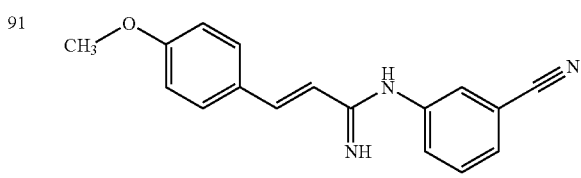 | D |
| 92 | 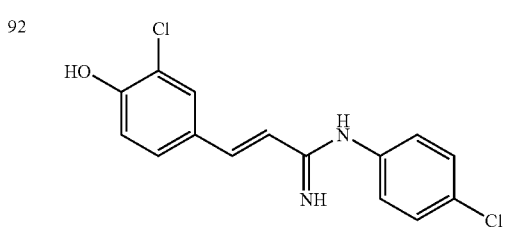 | D |
| 93 | 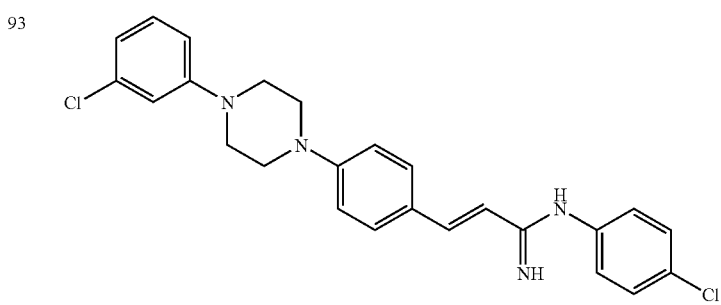 | D |
| 94 | 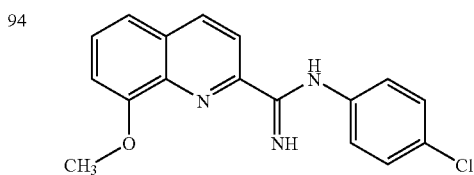 | D |

-continued
| Example | Chemical Structure | D₁ binding and D₂:D₁ Selectivity |
|---|---|---|
| 95 | 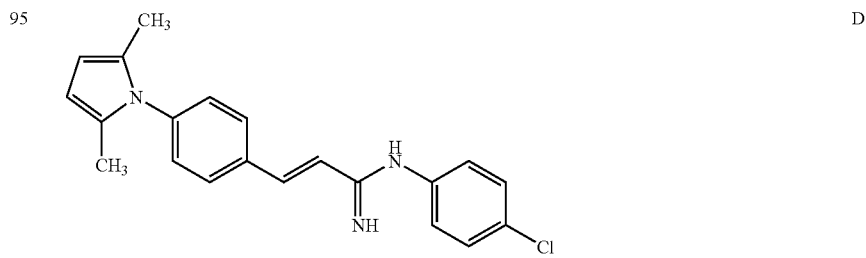 | D |
| 96 | 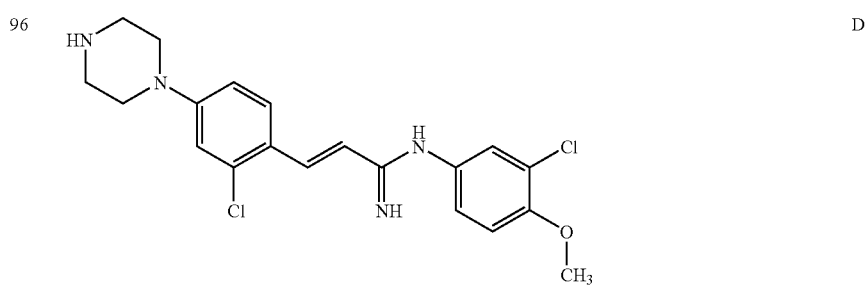 | D |
| 97 | 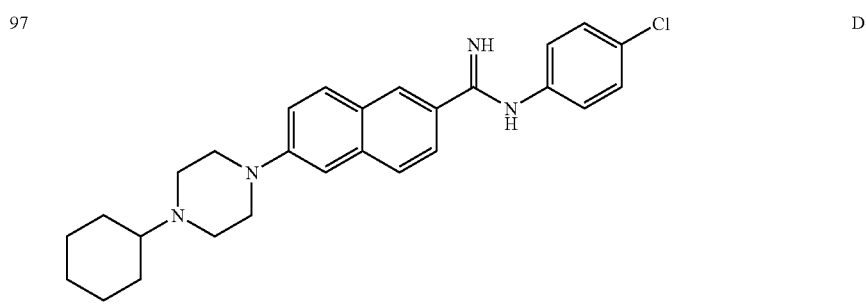 | D |
| 98 | 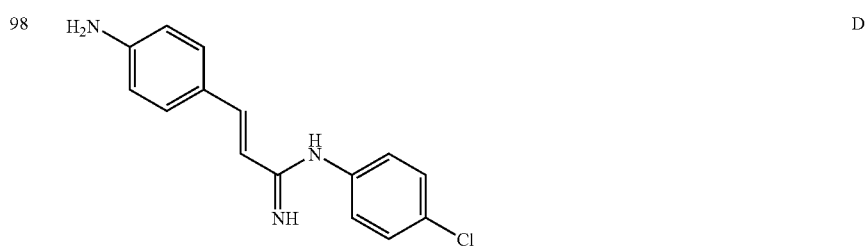 | D |
| 99 | 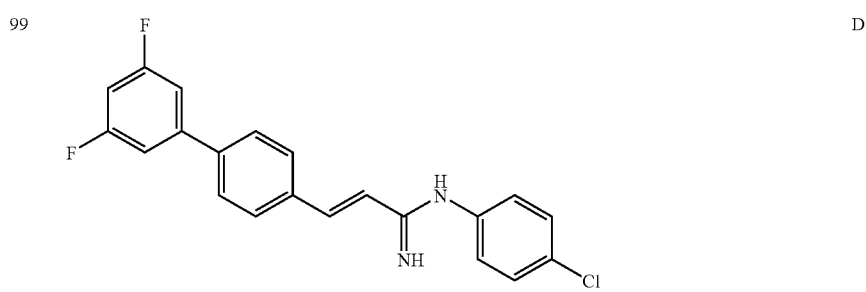 | D |

-continued
| Example | Chemical Structure | $D_1$ binding and $D_2:D_1$ Selectivity |
|---|---|---|
| 100 | 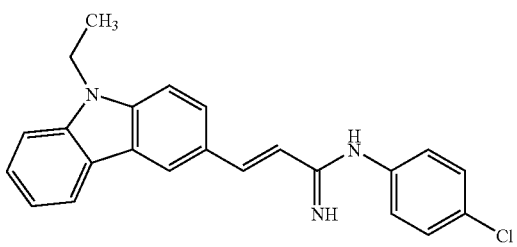 | D |
| 101 | 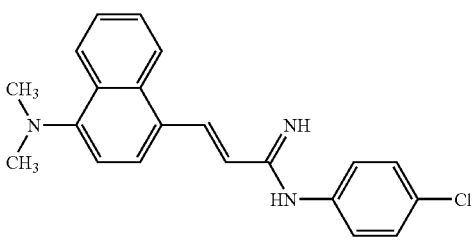 | D |
| 102 | 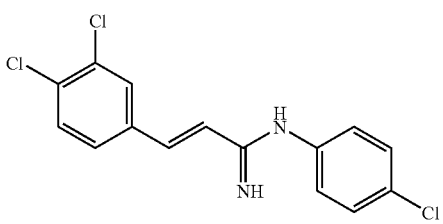 | D |
| 103 | 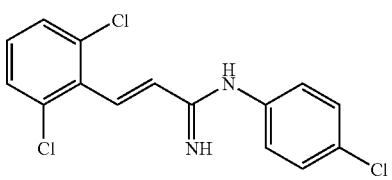 | D |
| 104 | 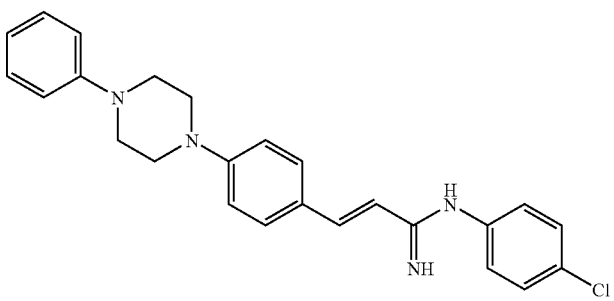 | D |
| 105 | 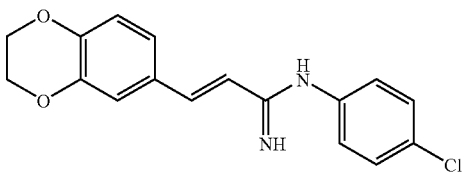 | D |

|Example|Chemical Structure|D₁ binding and D₂:D₁ Selectivity|
|---|---|---|
|106| 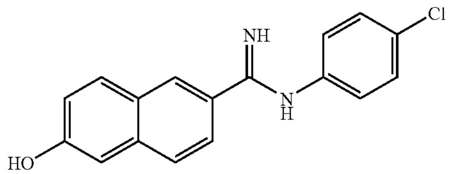 | D |
|107| 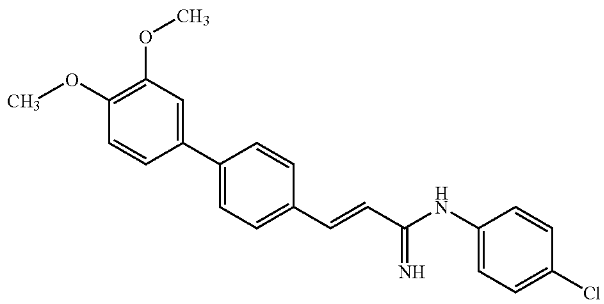 | D |
|108| 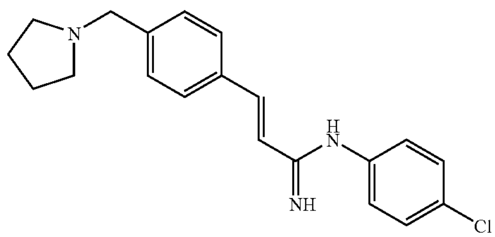 | D |
|109| 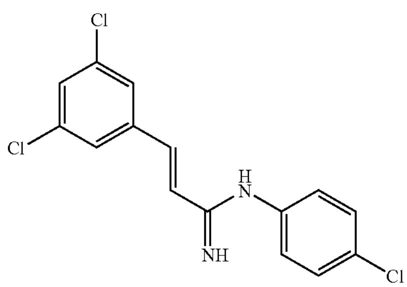 | D |
|110| 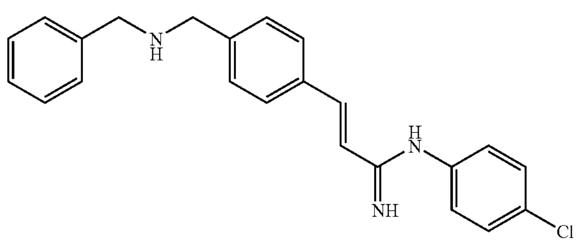 | D |
|111| 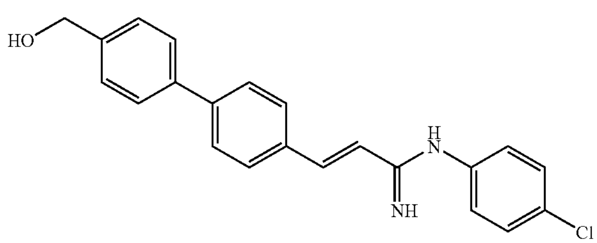 | D |

-continued

| Example | Chemical Structure | $D_1$ binding and $D_2$:$D_1$ Selectivity |
|---|---|---|
| 112 | 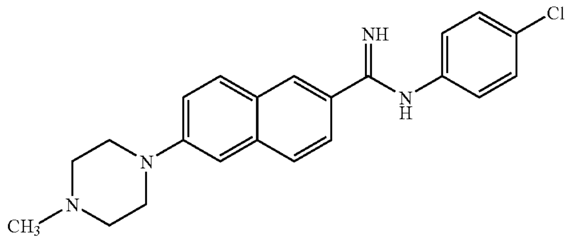 | D |
| 113 | 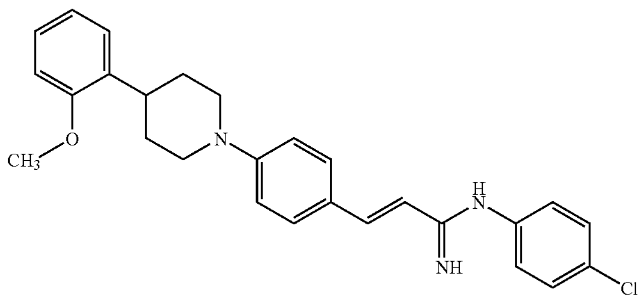 | D |
| 114 | 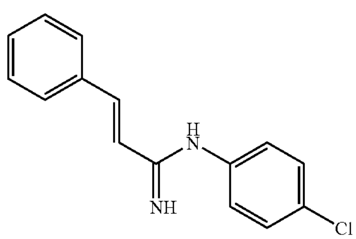 | D |
| 115 | 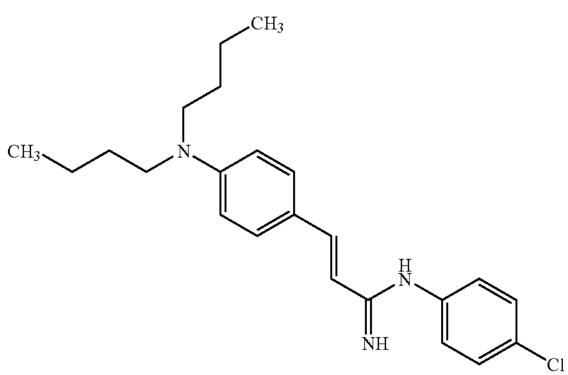 | D |
| 116 | 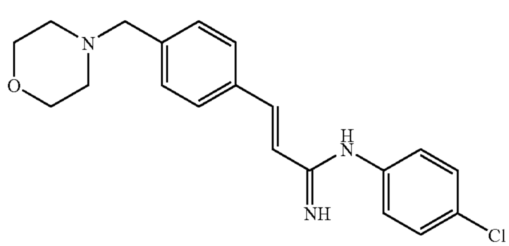 | D |

-continued
| Example | Chemical Structure | $D_1$ binding and $D_2:D_1$ Selectivity |
|---|---|---|
| 117 | 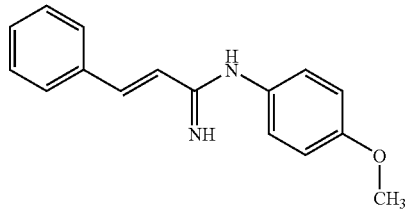 | D |
| 118 | 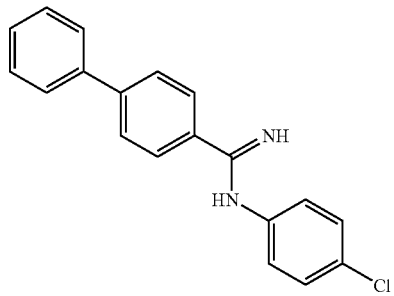 | D |
| 119 | 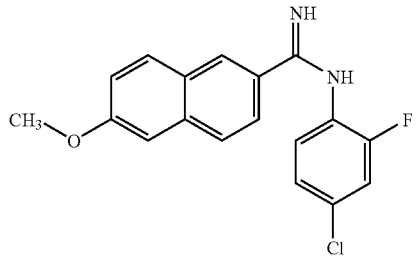 | D |
| 120 | 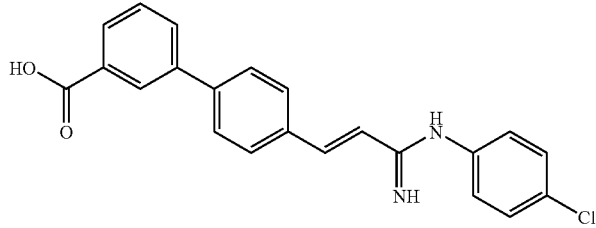 | D |
| 121 | 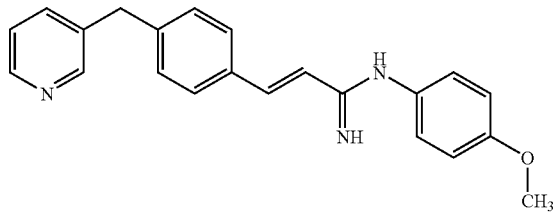 | D |

-continued

| Example | Chemical Structure | D₁ binding and D₂:D₁ Selectivity |
|---|---|---|
| 122 | 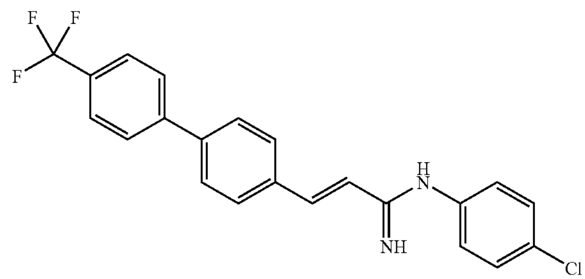 | D |
| 123 | 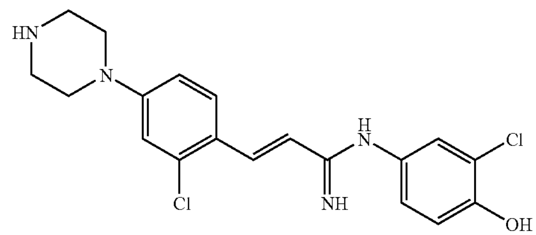 | D |
| 124 | 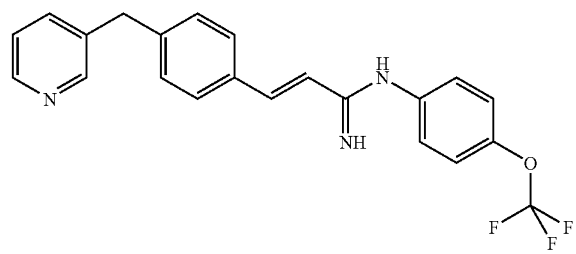 | D |
| 125 | 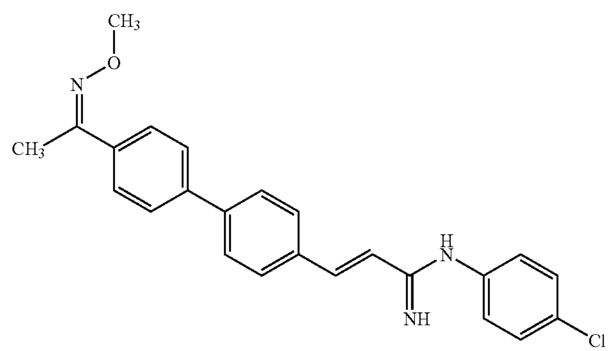 | D |
| 126 | 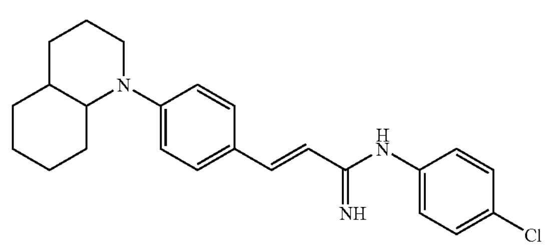 | D |

-continued
| Example | Chemical Structure | D₁ binding and D₂:D₁ Selectivity |
|---|---|---|
| 127 | 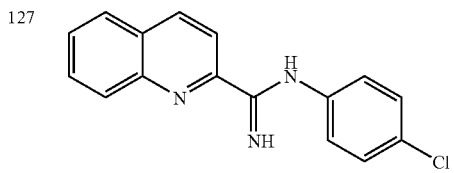 | D |
| 128 | 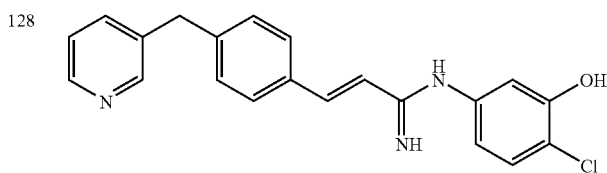 | D |
| 129 | 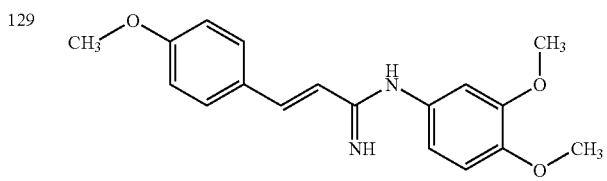 | D |
| 130 | 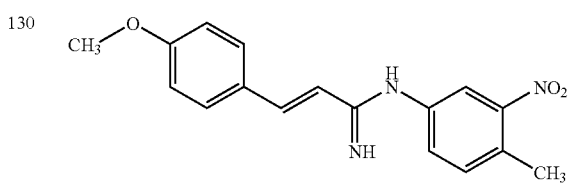 | D |
| 131 | 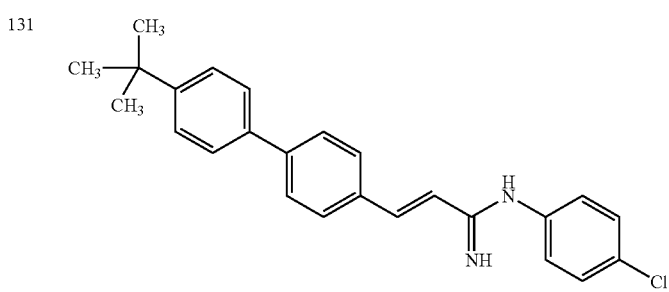 | D |
| 132 | 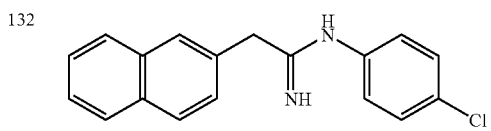 | D |
| 133 | 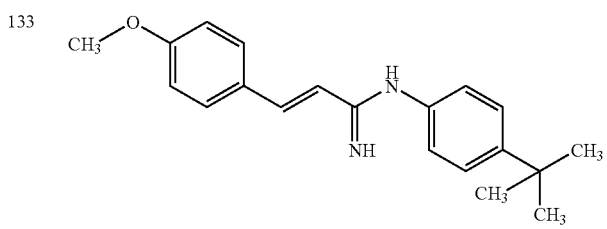 | D |

| Example | Chemical Structure | $D_1$ binding and $D_2$:$D_1$ Selectivity |
|---|---|---|
| 134 | 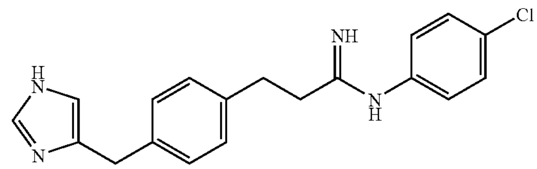 | D |

What is claimed is:

1. A compound having the structural formula I:

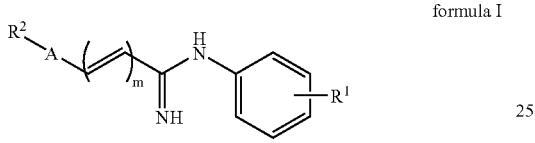
formula I or a pharmaceutically acceptable salt thereof, wherein

A is phenyl optionally substituted with 1 to 4 moieties which can be the same or different, each moiety being independently selected from the group consisting of halogen, alkyl, aryl, heteroaryl, heterocycloalkyl, cycloalkyl, —CF$_3$, —CN, —OCF$_3$, —OR$^{11}$, —(CR$^4$R$^5$)$_p$OR$^{11}$, —NR$^5$R$^6$, —(CR$^4$R$^5$)$_p$NR$^5$R$^6$, —C(O$_2$)R$^{11}$, —C(O)R$^{11}$, —C(O)NR$^5$R$^6$, —SR$^{11}$, —S(O$_2$)R$^{11}$, —S(O$_2$) NR$^5$R$^6$, —N(R$^5$)S(O$_2$)R$^7$, —N(R$^5$)C(O)R$^7$ and —N(R$^5$)C(O)NR$^5$R$^6$;

m is 0 or 1;
p is 1 to 4;

R$^1$ is 1 to 5 moieties independently selected from hydrogen, cycloalkyl, heterocyclyl, aryl, heteroaryl, halogen, hydroxy, alkoxy, —NR$^5$R$^6$, —SR$^{11}$, —CF$_3$, —OCF$_3$, —CN, —NO$_2$ and alkyl, or two adjacent R$^1$ moieties can be linked to form

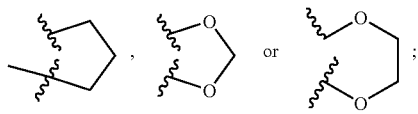

R$^2$ is 1 to 5 moieties independently selected from halogen, aryl, heteroaryl,

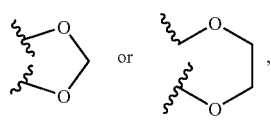, wherein each of said aryl or heteroaryl for R$^2$ can be optionally substituted with 1 to 4 moieties which can be the same or different, each moiety being independently selected from the group consisting of halogen, alkyl, aryl, cycloalkyl, alkylenyl, aralkyl, —C(O)H, —C(O)OH, —C(R$^4$)=NOR$^{11}$, —CF$_3$, —CN, —OCF$_3$, —OR$^{11}$, —(CR$^4$R$^5$)$_p$OR$^{11}$, —NR$^5$R$^6$, —(CR$^4$R$^5$)$_p$NR$^5$R$^6$, —C(O$_2$)R$^{11}$, —C(O)R$^{11}$, —C(O)NR$^5$R$^6$, —SR$^{11}$, —S(O$_2$)R$^{11}$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

R$^3$ is hydrogen, alkyl, —C(O)R$^{11}$, —SO$_2$R$^{11}$, —C(O)alkoxy, aryl, cycloalkyl, cycloalkylalkyl, heteroaryl, heterocyclylalkyl, heteroaralkyl or aralkyl, wherein each of said alkyl, aryl, cycloalkyl, cycloalkylalkyl, heteroaryl, heterocyclylalkyl, heteroaralkyl or aralkyl for R$^3$ can be optionally substituted with 1 to 4 moieties which can be the same or different, each moiety being independently selected from the group consisting of halogen, alkyl, aryl, cycloalkyl, —CF$_3$, —CN, —OCF$_3$, —OR$^{11}$, —(CR$^4$R$^5$)$_p$OR$^{11}$, —NR$^5$R$^6$, —(CR$^4$R$^5$)$_p$NR$^5$R$^6$, —C(O$_2$)R$^{11}$, —C(O)R$^{11}$, —C(O)NR$^5$R$^6$, —SR$^{11}$, —S(O$_2$)R$^{11}$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

R$^4$ is hydrogen or alkyl;

R$^5$ is hydrogen, alkyl or aryl, wherein each of said alkyl or aryl for R$^5$ can be unsubstituted or substituted with 1 to 4 moieties which can be the same or different, each moiety being independently selected from the group consisting of —CN, —NO$_2$, halogen, vinyl, alkoxy, —OCF$_3$, alkoxyalkyl, —C(O)OH, —C(O)O-alkyl, —CF$_3$ and alkyl;

R$^6$ is hydrogen, alkyl or aryl, wherein each of said alkyl or aryl for R$^6$ can be unsubstituted or substituted with 1 to 4 moieties which can be the same or different, each moiety being independently selected from the group consisting of —CN, —NO$_2$, halogen, vinyl, alkoxy, —OCF$_3$, alkoxyalkyl, —C(O)OH, —C(O)O-alkyl, —CF$_3$ and alkyl;

R$^7$ is selected from the group consisting of alkyl, cycloalkyl, aryl, heteroaryl, —CF$_3$, —OCF$_3$, aralkyl and heteroaralkyl wherein each of said alkyl, cycloalkyl, aryl, heteroaryl, aralkyl and heteroaralkyl for R$^7$ can be unsubstituted or substituted with 1 to 4 moieties which can be the same or different, each moiety being independently selected from the group consisting of halogen, alkyl, aryl, cycloalkyl. —CF$_3$, —OCF$_3$, —CN, —OR$^5$, —NR$^5$R$^{10}$, —CH$_2$OR$^5$, —C(O$_2$)R$^5$, —C(O)NR$^5$R$^{10}$, —C(O)R$^5$, —SR$^{10}$, —S(O$_2$)R$^{10}$, —S(O$_2$)NR$^5$R$^{10}$, —N(R$^5$)S(O$_2$)R$^{10}$, —N(R$^5$)C(O)R$^{10}$ and —N(R$^5$)C(O)NR$^5$R$^{10}$;

R8 is alkyl, aryl, heteroaryl, —NR³R⁴,

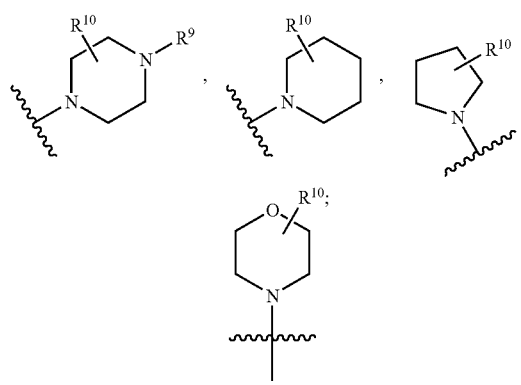

R⁹ is hydrogen. alkyl, —C(O)R¹¹, —SO₂R¹¹, aryl, cycloalkyl, cycloalkylalkyl, heteroaryl, heterocyclyl, heteroaralkyl or aralkyl, wherein each of said aryl, cycloalkyl, cycloalkylalkyl, heteroaralkyl or aralkyl for R⁹ can be unsubstituted or substituted with 1 to 4 moieties which can be the same or different, each moiety being independently selected from the group consisting of —CN, —NO₂, halogen, vinyl, alkoxy, —OCF₃, alkoxyalkyl, —C(O)OH, —C(O)O-alkyl, —CF₃ and alkyl:

R¹⁰ is hydrogen, alkyl or aryl, wherein each of said alkyl or aryl for R¹⁰ can be unsubstituted or substituted with 1 to 4 moieties which can be the same or different; each moiety being independently selected from the group consisting of —CN, —NO₂, halogen, vinyl, alkoxy, —OCF₃, alkoxyalkyl, —C(O)OH, —C(O)O-alkyl, —CF₃ and alkyl; and R¹¹ is alkyl or aryl, wherein each of said alkyl or aryl for R¹¹ can be unsubstituted or substituted with 1 to 4 moieties which can be the same or different, each moiety being independently selected from the group consisting of —CN, —NO₂. halogen, vinyl, alkoxy, —OCF₃, alkoxyalkyl, —C(O)OH, —C(O)O-alkyl, —CF₃ and alkyl.

2. The compound of claim 1 wherein

R³ is hydrogen or alkyl; and

R⁵ is hydrogen or alkyl.

3. The compound of claim 2 wherein

R³ is methyl or hydrogen; and

R⁵ is methyl or hydrogen.

4. A compound of formula I selected from the group consisting of

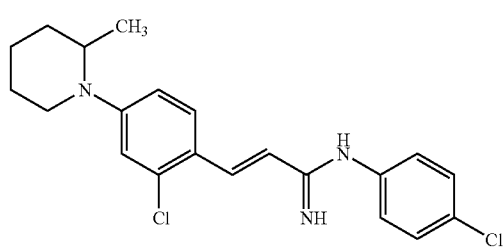

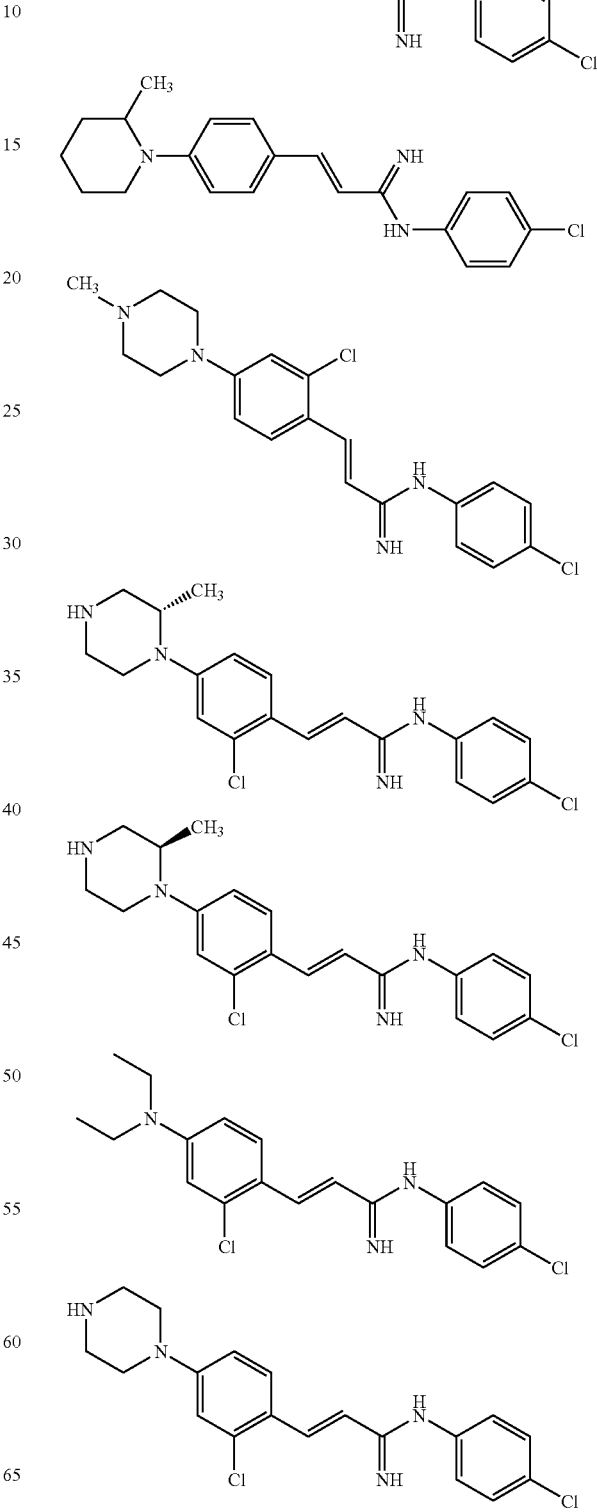

-continued

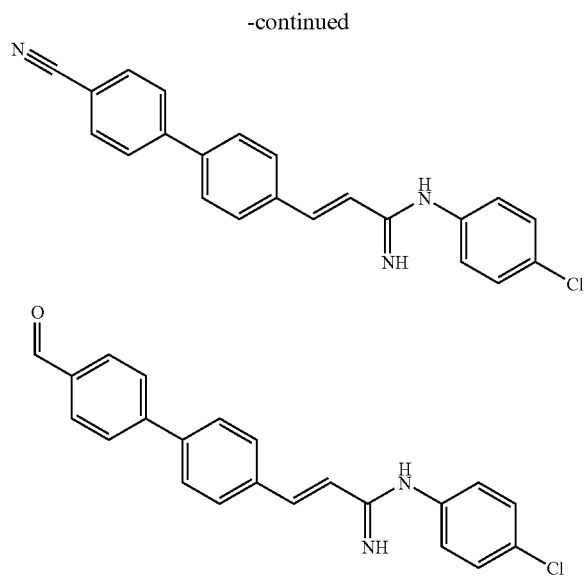

or a pharmaceutically acceptable salt thereof.

5. A compound of formula I selected from the group consisting of

-continued

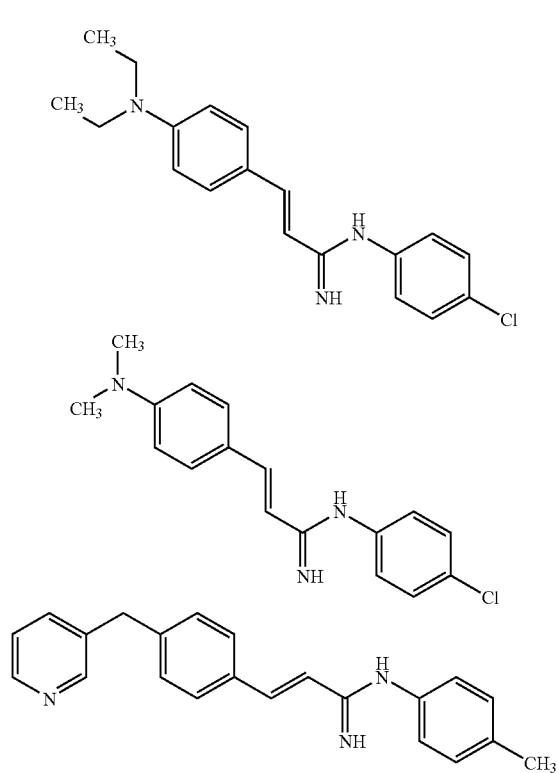

or a pharmaceutically acceptable salt thereof.

6. A pharmaceutical composition comprising a therapeutically effective amount of at least one compound of claim 1 in combination with at least one pharmaceutically acceptable carrier.

7. A pharmaceutical composition comprising a therapeutically effective amount of at least one compound of claim 4 in combination with at least one pharmaceutically acceptable carrier.

* * * * *